US007019111B2

(12) United States Patent
Sallberg

(10) Patent No.: US 7,019,111 B2
(45) Date of Patent: Mar. 28, 2006

(54) GLYCOSYLATED LIGAND/RECEPTOR SPECIFICITY EXCHANGERS SPECIFIC FOR BACTERIAL ADHESION RECEPTORS

(75) Inventor: Matti Sallberg, Alvsjo (SE)

(73) Assignee: Tripep AB, Huddinge (SE)

( * ) Notice: Subject to any disclaimer, the term of this patent is extended or adjusted under 35 U.S.C. 154(b) by 326 days.

(21) Appl. No.: 10/608,541

(22) Filed: Jun. 27, 2003

(65) Prior Publication Data

US 2004/0019189 A1 Jan. 29, 2004

Related U.S. Application Data

(63) Continuation of application No. 09/664,945, filed on Sep. 19, 2000, now Pat. No. 6,660,842, which is a continuation-in-part of application No. 09/532,106, filed on Mar. 21, 2000, now Pat. No. 6,245,895, which is a continuation of application No. 09/246,258, filed on Feb. 8, 1999, now Pat. No. 6,040,137, which is a continuation of application No. 08/737,085, filed as application No. PCT/SE95/00468 on Apr. 27, 1995, now Pat. No. 5,869,232.

(51) Int. Cl.
*A61K 38/00* (2006.01)

(52) U.S. Cl. ........................ 530/324; 530/325; 530/326; 530/350; 530/807; 530/825; 435/7.1; 435/7.2; 435/5

(58) Field of Classification Search .................. 435/7.1, 435/7.2, 5; 530/324–326, 350, 807, 825
See application file for complete search history.

(56) References Cited

U.S. PATENT DOCUMENTS

| | | | |
|---|---|---|---|
| 4,169,138 | A | 9/1979 | Jonsson |
| 4,376,110 | A | 3/1983 | David et al. |
| 4,471,058 | A | 9/1984 | Smith et al. |
| 4,486,530 | A | 12/1984 | David et al. |
| 4,589,881 | A | 5/1986 | Pierschbacher et al. |
| 4,946,778 | A | 8/1990 | Ladner et al. |
| 5,091,513 | A | 2/1992 | Huston et al. |
| 5,175,096 | A | 12/1992 | Hook et al. |
| 5,189,015 | A | 2/1993 | Hook et al. |
| 5,196,510 | A | 3/1993 | Rodwell et al. |
| 5,260,189 | A | 11/1993 | Formoso et al. |
| 5,320,951 | A | 6/1994 | Hook et al. |
| 5,416,021 | A | 5/1995 | Hook et al. |
| 5,440,014 | A | 8/1995 | Hook et al. |
| 5,561,049 | A | 10/1996 | Vold et al. |
| 5,571,511 | A | 11/1996 | Fischer |
| 5,571,514 | A | 11/1996 | Hook et al. |
| 5,582,975 | A | 12/1996 | Milliman |
| 5,601,830 | A | 2/1997 | Su et al. |
| 5,627,263 | A | 5/1997 | Ruoslahti et al. |
| 5,652,217 | A | 7/1997 | Hook et al. |
| 5,700,928 | A | 12/1997 | Hodgson et al. |
| 5,714,332 | A | 2/1998 | Lussow et al. |

(Continued)

FOREIGN PATENT DOCUMENTS

| | | | |
|---|---|---|---|
| EP | 0 182 546 | A2 | 5/1986 |
| EP | 0 508 427 | A | 10/1992 |
| JP | 9020798 | | 1/1997 |
| WO | WO 93/15210 | | 8/1993 |
| WO | WO 93/17044 | | 9/1993 |
| WO | WO 94/13804 | | 6/1994 |
| WO | WO 95/08577 | | 3/1995 |
| WO | WO 95/29938 | | 11/1995 |
| WO | WO 98/03543 | | 1/1998 |
| WO | WO 98/31389 | | 7/1998 |
| WO | WO 98/43677 | A1 | 10/1998 |
| WO | WO 99/27109 | | 6/1999 |
| WO | WO 99/61041 | A | 12/1999 |
| WO | WO 00/26385 | A | 5/2000 |
| WO | WO 95/22249 | A | 5/2000 |
| WO | WO 00/66621 | | 11/2000 |
| WO | WO 01/81421 | | 11/2001 |
| WO | WO 01/82546 | A1 | 11/2001 |
| WO | WO 02/24887 | | 3/2002 |

OTHER PUBLICATIONS

Barbas et al., "Assembly of combinatorial antibody libraries on phage surfaces: The gene III site," *Proc Natl Acad Sci USA*, 88:7978–7982, (1991).

Bianchi et al., "Chemical Synthesis of a Designed Beta–Protein through the Flow–Polyamide Method," *Int J Pept Protein Res*, 41(4):385–393 (1993).

Bianchi et al., "Afinity Purification of a Difficult–Sequence Protein: Implications for the Inclusion of Capping in Synthetic Protocols," *Int J Pept Protein Res*, 42(1):93–96 (1993).

Bichko et al., "Epitopes recognized by antibodies to denatured core protein of hepatitis B virus," *Mol. Immunol.*, 30(3):221–231, (1993).

Brett et al., "The invasin protein of Yersinia spp. Provides co–stimulatory activity to human T cells thorugh interaction with beta 1 integrins," *Eur. J. Immunol.*, 23(7):1608–1614 (1993).

Cello, J, et al., "Identification of group–common linear epitopes in structural and nonstructural proteins of enteroviruses by using synthetic peptides," *J. Clin. Microbiol.*, 31(4):911–916 (1993).

Chien et al., "Identification of group–common linear epitopes in structural and nonstructural proteins of enteroviruses by using synthetic peptides," *Proc Natl Acad Sci USA*, 88:9578–9582 (1991).

(Continued)

*Primary Examiner*—Jeffrey Stucker

(74) *Attorney, Agent, or Firm*—Knobbe, Martens, Olson & Bear, LLP

(57) ABSTRACT

The present invention generally relates to compositions and methods for preventing and treating human diseases including, but not limited to, pathogens such as bacteria, yeast, parasites, fungus, viruses, and cancer. More specifically, embodiments described herein concern the manufacture and use of ligand/receptor specificity exchangers, which redirect existing antibodies in a subject to receptors present on pathogens.

21 Claims, No Drawings

U.S. PATENT DOCUMENTS

| | | | |
|---|---|---|---|
| 5,766,857 | A | 6/1998 | Ruoslahti et al. |
| 5,766,951 | A | 6/1998 | Brown |
| 5,770,208 | A | 6/1998 | Fattom et al. |
| 5,770,702 | A | 6/1998 | Hook et al. |
| 5,776,712 | A | 7/1998 | Kuusela et al. |
| 5,789,549 | A | 8/1998 | Hook et al. |
| 5,840,846 | A | 11/1998 | Hook et al. |
| 5,843,774 | A | 12/1998 | Ginsberg |
| 5,846,536 | A | 12/1998 | Bissell et al. |
| 5,866,541 | A | 2/1999 | Hook et al. |
| 5,869,232 | A | 2/1999 | Sällberg |
| 5,888,738 | A | 3/1999 | Hendry |
| 5,922,548 | A | 7/1999 | Lussow et al. |
| 5,929,220 | A | 7/1999 | Tong et al. |
| 5,939,273 | A | 8/1999 | Lussow et al. |
| 5,942,606 | A | 8/1999 | Lal et al. |
| 5,955,078 | A | 9/1999 | Burnham et al. |
| 5,980,908 | A | 11/1999 | Hook et al. |
| 5,981,274 | A | 11/1999 | Tyrell et al. |
| 6,008,341 | A | 12/1999 | Foster et al. |
| 6,030,613 | A | 2/2000 | Blumberg et al. |
| 6,040,137 | A | 3/2000 | Sällberg |
| 6,066,648 | A | 5/2000 | Duggan et al. |
| 6,077,677 | A | 6/2000 | Hodgson et al. |
| 6,086,875 | A | 7/2000 | Blumberg et al. |
| 6,086,895 | A | 7/2000 | Hook et al. |
| 6,087,330 | A | 7/2000 | Kogan et al. |
| 6,090,388 | A | 7/2000 | Wang |
| 6,090,944 | A | 7/2000 | Hutchinson |
| 6,093,539 | A | 7/2000 | Maddon et al. |
| 6,245,985 | B1 | 6/2001 | Sasaki et al. |
| 6,417,324 | B1 | 7/2002 | Sällberg |
| 6,485,726 | B1 | 11/2002 | Blumberg et al. |
| 2002/0025513 | A1 | 2/2002 | Sällberg |
| 2002/0058247 | A1 | 5/2002 | Sällberg |
| 2003/0021789 | A1 | 1/2003 | Xu et al. |
| 2003/0044418 | A1 | 3/2003 | Davis et al. |

OTHER PUBLICATIONS

Cohen, J., et al., "Ligand binding to the cell surface receptor for reovirus type 3 stimulates galactocerebroside expression by developing oligodendrocytes," *Proc. Natl. Acad. Sci. USA*, 87(13):4922–4926 (1990).

Colberre–Garapin et al., "A new dominant hybrid selective marker for higher eukaryotic cells," *J. Molecular Biology*, 150:1 (1981).

Database Genseq 'Online! Oct. 21, 1991, Asahi Chemical Ind. KK: "L–chain variable region of plasminogen activator antibody" XP002183673, Accession AAP61027 (published in JP11729000).

Database Genseq 'Online! Jan. 8, 1993, Clonatec SA: "Hepatitis B irus HBc antigen II," XP002183674, Accession AAR25272 (published in EP494825).

Database Genseq 'Online! Jul. 1, 1993, Cytel Corp: "Cytotoxic T–lymphocyte inducing peptide 802.03." XP002183675, Accession AAR33488.

Database WPI, Section Ch., Week 199713, Derwent Publications Ltd., London, GB: Class B04, AN 1997–140911, XP002183678 & JP 09 020798 A (Asahi Kasei Kogyo KK) Jan. 21, 1997, abstract.

Database Patent_PRT 'Online! Mar. 21, 2001, Eurodiagnostica AB: "Sequance 9 from Patent W)0116163" XP002183677, Accession AX 090806.

Database Genseq 'Online! Jul. 31, 2000, Yeda Res & Dev Co Ltd: "Murine anti–Pab–421 IDI–1 mAb heavy chain CDR based Peptide IDI–H1", XP002183676, Accession AAY70799 (published in WO0023082).

Doolittle et al., "The amino Acid Sequence of the alpha–Chain of Human Fibrinogen." *Nature*, 280(5722):464–468, (1979).

Felding–Habermann et al., "Role of β3 Integrins in Melanoma cell Adhesion to Activated Platelets under Flow," *J. Biol. Chem.*, 271(10):5892–5900 (1996).

Flock, "Extracellular–Matrix–Binding Proteins as Targets for the Prevention of Staphylococcus Aureus Infections," *Molecular Medicine Today*, 5(12):532–537 (1999).

Ganem, "Hepadnaviridae and their replication," *Fields Virology*, Third Ed., pp. 2703–2705 (1996).

GenCore Sequence Alignment of Sequence ID No: 16 with the L–chain variable region of plasminogen activator antibody of JP61172900–A, Ashi Chemical Ind. KK. (Apr. 8, 1986) ID NO: p. 61027.

Grabowska et al., "Identification of type–specific domains within glycoprotein G of herpes simplex virus type 2 (HSV–2) recognized by the majority of patients infected with HSV–2, but not by those infected with HSV–1," *Journal of General Virology*, 80(pt.7):1789–1798 (1999).

Greenspan et al., Nature Biotechnology, 7:936–937 (1999).

Haseltine, "Replication and Pathogenesis of the AIDS Virus," *Journal of Acquired Immune Deficiency Syndromes*, 1(3):217–240 and 231–236, (1988).

Henschen et al., "Amino acid sequence of human fibrin. Preliminary note on the Completion of the β–Chain Sequence," *Z. Physiol. Chem.*, 358(12):1643–1646 (1977).

Holliger et al., "Diabodies': Small Bivalent and Bispecific Antibody Fragments," *Proc Natl Acad Sci USA*, 90(14):6444–6448, (1993).

Huse et al., "Generation of a large combinatorial library of the immunoglobulin repertoire in Phage Lambda," *Science*, 256:1275–1281 (1989).

Jin et al., "Expression, Isolation, and Characterization of the Hepatitis C Virus ATPase/RNA Helicase," *Archives of Biochemistry and Biophysics*, 323:47–53 (1995).

Katada et al., "A Novel Peptide Motif for Platelet Fibrinogen Receptor Recognition," *J. Biol. Chem.*, 272(12):7720–7726 (1997).

Kreitman et al., "Immunotoxins for targeted cancer therapy," Advanced Drug Delivery Reviews, 31:53–88 (1998).

Korba and Gerin, "Generation of a large combinatorial library of immunoglobulin repertoire in Phage Lambda," Science, 256:1275–1281 (1989).

Korba and Milman, "A cell cultrue assay for compounds which inhibit hepatitis B virus repolication," Antiviral Res, 15(3):217–228 (1991).

Lazdina et al., Journal of Virology, 75(14):6367–6374 (2001).

Leanna & Hannink, "The reverse two–hybrid system: a genetic scheme for selection against specific protein/protein interactions," *Nucl. Acid Res.*, 24:3341–3347 (1996).

Lee et al., "Predominant Etiologic Association of Hepatitis C Virus with Hepatocellular Carcinoma Compared with Hepatitis B Virus in Elderly Patients in a Hepatitis B–Endemic Area," *Cancer*, 72:2564–2567.

Levi et al., "A complementarity–determining region synthetic peptide acts as a miniantiody and neutralizes human immunodeficiency virus type 1 in vitro," *Proc Natl Acad Sci USA*, 90(10):4374–4378, (1993).

Lew et al., "Site–directed immune responses in DNA vaccines encoding ligand–antigen fusions," *Vaccine*, England, vol. 18, No. 16, pp. 1681–1685 (2000).

Lottspeich et al., "Amino acid sequence of human fibrin. Preliminary note on the Completion of the gamma–Chain Sequence," *Z. Physiol. Chem.*, 358(7):935–938 (1977).

Lowman HB, "Bacteriophage display and discovery of peptide leads for drug development," *Annu. Rev. Biophys. Biomol. Struct.*, 26:401–424 (1997).

Machida et al., "Antigenic sites on the arginine–rich carboxyl–terminal doman of the capsid protein of hepatitis B virus distinct form hepatitis B core or e antigen," Mol. Immunol. 26(4):421–431 (1989).

McDevvit et al., "Characterization of the interaction between the *Staphylococcus aureus* clumping factor (ClfA) and fibrinogen," *Eur. J. Biochem.*, 247(1):416–424 (1997).

McDevvit et al., "Identification of the ligand–binding domain of the surface–located fibrinogen receptor (clumping factor) of *Staphylococcus aureus*," Molecular Microbiology, vol. 16, No. 5, pp. 895–907 (1995).

Milich et al., "The humoral immune response in acute and chronic hepatitis B virus infection," *Springer Semin. Immunopathol.*, 17:149–166 (1995).

Milich et al, "The Nucleocapsid of Hepatitis B Virus is both a T–Cell–Independent Antigen", *Science*, 234:1398–1401 (1986).

Milich et al., "Role of B cells in antigen presentation of the hepatitis B core," *Proc. Natl. Acad. Sci. USA*, 94:14648–14653 (1997).

Mollick, et al., "Localization of a Site on Bacterial Superantigens that Determines T Cell Receptor ∃ Chain Specificity," J. Exp. Med., 177:283–293 (1993).

Morrison et al., "Chimeric human antibody molecules: mouse antigen–binding domains with human constant region domains," *Proc Natl Acad Sci USA*, 81(21):6851–6855 (1984).

Neuberger et al., "Recombinant antibodies possessing novel effector functions," *Nature*, 312:604–608 (1984).

Ogg, et al., "Sensitization of tumour cells to lysis by virus–specific CTL using antibody–targeted MHC class I/peptide complexes," British Journal of Cancer, 82(5):1058–1062 (2000).

Owens et al., "Mapping the Collagen–Binding Site of Human Fibronectin by Expression in *Escherichia coli*," Embo Journal, IRL Press, Eynsham, GB, vol. 5, No. 11, pp. 2825–2830 (1986).

Pei et al., "Functional Studies of a Fibrinogen Binding Protein from Staphylococcus Epidermidis," *Infection and Immunity*, 67(9):4525–4530 (1999).

Prange et al., Journal of Biological Chemistry, 380(3):305–314 (1999).

Roivanen et al., "Antigenic regions of poliovirus type 3/Sabin capsid proteins recognized by human sera in the peptide scanning technique," *Virology*, 180:99–107 (1991).

Rüther and Müller–Hill, "Easy identification of cDNA clones," *EMBO Journal*, 2(10):1791–1794 (1983).

Salfeld et al., "Antigenic determinants an dfunctional domains in core antigen and e antigen from hepatitis B virus," Journal of Virology, 63(2):798–808 (1989).

Sallberg et al., "Characterization of a linear binding site for a monoclonal antibody to hepatitis B core antigen," J. Med Virol., 33(4):248–252 (1991).

Sallberg et al., "Immunochemical structure of the carboxy–terminal part of hepatitis B e antigen: identification of internal and surface–exposed sequences," *Journal of General Virology*, 74:1335–1340 (1993).

Sallberg et al., "Human and murine B–cells recognize the HBeAg/beta (or HBe2) epitope as a linear determinant," Mol. Immunol., 28(7):719–726 (1991).

Sallberg et al., "Rapid 'tea–bag' peptide synthesis using 9–fluorenylmethoxcarbonyl (Fmoc) protected amino acids applied for antigenic mapping of viral proteins," *Immunology Letters*, 30:59–68 (1991).

Sallberg et al., "Synthetic peptides as mini antibodies," Peptides: Chemistry and Biology, eds. Hodges, R. and J. Rivier, ESCOM, Leiden, pp. 715–718 (1993).

Sällberg et al., "The Antigen/Antibody Specificity Exchanger: A New Peptide Based Tool for Re–directing Antibodies of Other Specificities to Recognize the V3 Domain of HIV–1 GP120," *Biochemical and Biophysical Research Communications*, 205:1386–1390 (1994).

Sällberg, M. "Ligand/Receptor Specificity Exchangers that Redirect Antibodies to Receptors on a Pathogen," U.S. Appl. No. 09/664,025, filed Sep. 19, 2000.

Sällberg, M. "Ligand/Receptor Specificity Exchangers that Redirect Antibodies to Receptors on a Pathogen," U.S. Appl. No. 09/664,945, filed Sep. 19, 2000.

Sällberg, "Synthetic Peptides That Bind to the Hepatitis B Virus Core and E Antigens," U.S. Appl. No. 10/153,271, filed May 21, 2002.

Saragovi et al., "Design and Synthesis of a Mimetic from an Antibody Complementarity–Determining Region," *Science*, 253(5021):792–795 (1991).

Schodel et al., "Structure of Hepatitis B Virus Core and e–antigen," *The Journal of Biological Chemistry*, 268:1332–1337 (1993).

Sequence alignment of Genseq sequence alignment of instant SEQ. ID No.: 28 with the antihuman parathyroid hormone–related protein of JP04228089–A, Kaneka Corp., (Aug. 18, 1992), ID No.: AR27008.

Sequence alignment of Genseq sequence alignment of instant SEQ. ID No.: 29 with anti DNA antibody 7b3 heavy chain variable region of WO 96/36361–a1. University of Michigan, (Aug. 12, 1997) ID No.: AAW04593.

Sequence alignment of Genseq sequence alignment of instant SEQ. ID No.: 33 with anti–proenkephalin antibody PE–19 of WO 9606863, University of Dundee (Oct. 9, 1996) ID No.: AAR91370.

Skrivelis et al., Scand. J. Immunol., 37:637–643 (1993).

Steinbergs et al., Proceedings of the Latvian Academy of Sciences, Section B, 50(2):74–77 (1996).

Takahashi et al., "Acute hepatitis in rates expressing human hepatitis B virus transgenes," Proc. Natl. Acad. Sci USA, 92:1470–1474 (1995).

Takeda et al., "Construction of chimaeric processed immunoglobulin genes containing mouse variable and human constant regionsequences," *Nature*, 314:452–454 (1985).

Taub, R., et al., "A monoclonal antibody against the platelet fibrinogen receptor contains a sequence that mimics a receptor recognition domain in fibronigen," *J. Biol. Chem.*, 264(1):259–265 (1989).

Tramontano et al., "The making of the minibody: an engineered β–protein for the display of conformationally constrained peptides," *J. of Molecular Recognition*, 7(1):9–24 (1994).

Watt et al., "Amino Acid Sequence of the β Chain of Human Fibrinogen," *Biochemistry*, 18(1):68–76 (1979).

Watt et al., "Amino acid sequence studies on the alpha chain of human fibrinogen overlapping sequences providing the complete sequence," *Biochemistry*, 18(24):5410–5416 (1979).

Williams et al., "Design of bioactive peptides based on antibody hypervariable region structures. Development of conformationally constrained and dimeric peptides with enhanced affinity," *J. Biol. Chem.*. , 266(8):5182–5190 (1991).

Williams et al., "Development of biologically active peptides based on antibody structure," *Proc Natl Acad Sci USA*, 86(14):5537–5541 (1989).

Winter and Milstein, "Man–made antibodies," *Nature*, 349(6307):293–299 (1991).

Wood et al., Veterinary Immunology and Immunopathology, 54(1–4):33–44 (1999).

Zanetti, "Antigenized Antibodies," *Nature*, 355:476–477 (1992).

Zhang et al., "Characterization of a monoclonal antibody and its single–chain antibody fragment recognizing the nucleotide triphosphatase/helicase domain of the hepatitis C virus nonstructural 3 protein," *Clin. Diag. Lab. Immunol.*, 7(1):58–63 (2000).

Zhang et al., "Molecular basis for antibody cross–reactivity between the hepatitis C virus core protein and the hos–derived GOR protein," *Clin. Exp. Immunol.*, 6(33):403–409 (1994).

Chui et al., "Genetic remodeling of protein glycosylation in vivo induces autoimmune disease," PNAS, 98(3):1142–1147 (2001).

Ennas et al., "The Human ALL–1/MII/HRX Antigen is Predominantly Localized in the Nucleus of Resting and Proliferating Peripheral Blood Mononuclear Cells" Cancer Research 57, 2035–2041, May 15, 1997.

Galili et al., "Evolutionary relationship between the natural anti–Gal antibody and the Galα1→3Gal epitope in primates" Proc. Natl. Acad. Sci. vol. 84, pp. 1369–1373, Mar. 1987 Immunology.

Galili et al., Human natural anti–α–galactosyl IgG: the specific recognition of α(1→3)–linked galactose residues, J. Exp. Med., vol. 162, Aug. 1985, pp. 573–582.

Galili et al., "One percent of human ciculating B Lymphocytes are capable of producing the natural anti–gal antibody" Blood, vol. 82, No. 8, Oct. 15, 1993 pp. 2485–2493.

Leibiger et al. (1998) Structural characterization of the oligosaccharides of a human monoclonal anti–lipopolysaccharide immunoglobulin M. Glycobiology, 8(5):497–507.

Li et al., "Adenovirus–mediated expression of pig α(1,3) galactosyltransferase reconstructs Gal α(1, 3) Gal epitope on the surface of human tumor cells," Cell Research, 11(2):116–124 (2001), http://www.cell–research.com/20012/01–2–xl.html.

Lin et al. (1998) Differential recognition by proteins of α–galactosyl residues on endothelial cell surfaces. Glycobiology. 8(5):433–443.

Mizukami et al. (1988) Binding region for human immunodeficiency virus (HIV) and epitopes for HIV–blocking monoclonal antibodies of the CD4 molecule defined by site–directed mutagenesis. Proc. Natl. Acad. Sci. 85:9273–9277.

Ramberg, "The Nutrition Science Site: Glyconutritionals," http://glycoscience.com/glycoscience/document__viewer.wm?&ID=719 (2000).

Randell et al., "High–throughput Chemistry toward Complex Carbohydrates and Carbohydrate–like Compoundsa," http://www.bentham.org/sample–issues/cchts5–2/arya/arya–ms.htm.

Rudd et al., "Glycosylation and the Immune System," Science, 291:2370–2376 (2001) http://sciencemag.org.

Rudd et al., "The role of glycosylation in the immune system and inflammation," *Research Groups–Dept. of Biochemistry, Oxford*, http://www.bioch.ox.ac.uk/rgroups/rgroupsnew.asp?Group__ID=40.

Sears et al., "Toward Automated Synthesis of Oligosaccharides and Glycoproteins," Science, vol. 291, pp. 2344–2350, Mar. 23, 2001, http://www.sciencemag.org.

Signals Magazine: Buzz—Glycosylation Matters Jun. 6, 2002, http://www.signalsmag.com/signalsmag.nsf/0/A08BFCD79126B34F88256BCE0011B41A.

The Columbia Encyclopedia, Sixth Edition, Copyright 2002, Columbia University Press, http://www.bartleby.com/65/gl/glycopro.html.

Tramontano et al., "The Making of the Minibody: An Engineered Beta–Proten for the Display of Conformationally Constrained Peptides," *Journal of Molecular Recognition*, 7(1):9–24 (1994).

GLYCOSYLATED LIGAND/RECEPTOR SPECIFICITY EXCHANGERS SPECIFIC FOR BACTERIAL ADHESION RECEPTORS

CROSS-REFERENCE TO RELATED APPLICATIONS

This application is a continuation of U.S. patent application Ser. No. 09/664,945, filed on Sep. 19, 2000, now U.S. Pat. No. 6,660,842, which is a continuation-in-part of U.S. patent application Ser. No. 09/532,106, filed on Mar. 21, 2000, now U.S. Pat. No. 6,245,895; which is a continuation of U.S. patent application Ser. No. 09/246,258, filed on Feb. 8, 1999, now U.S. Pat. No. 6,040,137; which is a continuation of U.S. patent application Ser. No. 08/737,085, filed on Dec. 27, 1996, now U.S. Pat. No. 5,869,232; which was a national phase application of PCT/SE 95/00468, filed on Apr. 27, 1995 that designated the United States of America and was published in English, and claimed priority to Swedish patent application Ser. No. 9401460, filed on Apr. 28, 1994. This application claims priority to U.S. patent application Ser. Nos. 09/664,945; 09/532,106; 09/246,258; 08/737,085; PCT/SE 95/00468; and Swedish patent application Ser. No. 9401460, all of which are hereby expressly incorporated by reference in their entireties.

FIELD OF THE INVENTION

The present invention generally relates to compositions and methods for preventing and treating human diseases including, but not limited to, pathogens such as bacteria, yeast, parasites, fungus, viruses, and cancer. More specifically, embodiments described herein concern the manufacture and use of ligand/receptor specificity exchangers, which redirect existing antibodies in a subject to receptors present on pathogens.

BACKGROUND OF THE INVENTION

Infection by pathogens, such as bacteria, yeast, parasites, fungus, and viruses, and the onset and spread of cancer present serious health concerns for all animals, including humans, farm livestock, and household pets. These health threats are exacerbated by the rise of strains that are resistant to vaccination and/or treatment. In the past, practitioners of pharmacology have relied on traditional methods of drug discovery to generate safe and efficacious compounds for the treatment of these diseases. Traditional drug discovery methods typically involve blindly testing potential drug candidate-molecules, often selected at random, in the hope that one might prove to be an effective treatment for some disease. With the advent of molecular biology, however, the focus of drug discovery has shifted to the identification of molecular targets associated with the etiological agent and the design of compounds that interact with these molecular targets.

One promising class of molecular targets are the receptors found on the surface of bacteria, yeast, parasites, fungus, viruses, and cancer cells, especially receptors that allow for attachment to a host cell or host protein (e.g., an extracellular matrix protein). Research in this area primarily focuses on the identification of the receptor and its ligand and the discovery of molecules that interrupt the interaction of the ligand with the receptor and, thereby, block adhesion to the host cell or protein. Although several receptor antagnosists have promising therapeutic potential, there still remains a need for new compositions and methods to treat and prevent infection by pathogens and other diseases.

BRIEF SUMMARY OF THE INVENTION

The invention described herein concerns the manufacture, characterization, and use of novel agents that bind receptors on pathogens and redirect antibodies present in a subject to the pathogen. Embodiments include a ligand/receptor specificity exchanger having at least one specificity domain comprising a ligand for a receptor and at least one antigenic domain joined to said specificity domain, wherein said antigenic domain comprises an epitope of a pathogen or toxin.

Some embodiments of the ligand/receptor specificity exchanger have a specificity domain that comprises at least three consecutive amino acids of a peptide selected from the group consisting of an extracellular matrix protein, a ligand for a receptor on a virus, and a ligand for a receptor on a cancer cell. In some aspects of this embodiment, for example, the peptide is an extracellular matrix protein selected from the group consisting of fibrinogen, collagen, vitronectin, laminin, plasminogen, thrombospondin, and fibronectin. Preferably, the extracellular matrix protein comprises at least 3 amino acids of the alpha-chain of fibrinogen and in the most preferred embodiments the ligand comprises the sequence Arginine-Glycine-Aspartate (RGD).

In other embodiments, the peptide described above is a ligand for a receptor on a virus selected from the group consisting of T4 glycoprotein and hepatitis B viral envelope protein. In still other aspects of this embodiment, the peptide is a ligand for a receptor on a cancer cell selected from the group consisting of a ligand for HER-2/neu and a ligand for an integrin receptor. Preferred embodiments have a specificity domain that comprises a sequence provided by one of SEQ. ID. Nos. 1–42.

The ligand/receptor specificity exchangers described herein interact with a receptor found on a pathogen. In some embodiments, the receptor is a bacterial adhesion receptor, for example, a bacterial adhesion receptor selected from the group consisting of extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein.

The ligand/receptor specificity exchangers described herein also interact with a an antibody present in a subject. In some embodiments, for example, the antigenic domain comprises at least three amino acids of a peptide selected from the group consisting of a herpes simplex virus protein, a hepatitis B virus protein, a TT virus protein, and a poliovirus protein. In desirable embodiments, the ligand/receptor specificity exchanger has an antigenic domain that is a herpes simplex virus protein comprising a sequence selected from the group consisting of SEQ. ID. No. 53 and SEQ. ID. No. 54. In other desired embodiments, the antigenic domain is a hepatitis B virus protein comprising a sequence provided by one of SEQ. ID. No. 49, SEQ. ID. No. 50, SEQ. ID. No. 52, and SEQ. ID. No. 59.

Some ligand/receptor specificity exchangers also have an antigenic domain that is a TT virus protein comprising a sequence provided by one of SEQ. ID. Nos. 43–47 and SEQ. ID. Nos. 55–58. The ligand/receptor specificity exchangers can also have an antigenic domain that is a polio virus protein comprising a sequence selected from the group consisting of SEQ. ID. No. 48 and SEQ. ID. No. 51. Preferably, the ligand/receptor specificity exchanger has an antigenic domain that interacts with a high-titer antibody. In some embodiments, for example, the antigenic domain specifically binds to an antibody present in animal serum that has been diluted to between approximately 1:100 to 1:1000 or greater. The specificity exchangers of SEQ. ID. Nos. 60–105 are embodiments of the invention.

Aspects of the invention also concern methods of treating or preventing a infection or proliferation of a pathogen. One approach for example, involves a method for treating and preventing bacterial infection. This method is practiced by providing a therapeutically effective amount of a ligand/receptor specificity exchanger to a subject, wherein said ligand/receptor specificity exchanger comprises a specificity domain that has a ligand that interacts with a receptor on a bacteria, and an antigenic domain that comprises an epitope for a pathogen or toxin. A method of treating or preventing viral infection is also an embodiment. Accordingly, a method of treating or preventing a viral infection is practiced by providing a therapeutically effective amount of a ligand/receptor specificity exchanger to a subject, wherein said ligand/receptor specificity exchanger comprises a specificity domain that has a ligand that interacts with a receptor on a virus, and an antigenic domain that comprises an epitope for a pathogen or toxin. Similarly, a method of treating or preventing cancer is an embodiment and this method can be practiced by providing a therapeutically effective amount of a ligand/receptor specificity exchanger to a subject, wherein said ligand/receptor specificity exchanger comprises a specificity domain that has a ligand that interacts with a receptor on a cancer cell, and an antigenic domain that comprises an epitope for a pathogen or toxin.

DETAILED DESCRIPTION OF THE INVENTION

The following describes the manufacture, characterization, and use of novel agents that bind receptors on pathogens and redirect antibodies present in a subject to the pathogen. The embodiments are collectively referred to as "ligand/receptor specificity exchangers". The term "ligand/receptor specificity exchangers" refers a specificity exchanger that comprises a "specificity domain" that has at least one ligand for a receptor (a "ligand" is not an antibody or portion thereof) joined to an "antigenic domain" that has at least one epitope of a pathogen or toxin (e.g., pertussis toxin or cholera toxin).

The ligand/receptor specificity exchangers can comprise more than a specificity domain and an antigenic domain. For example, some ligand/receptor specificity exchangers comprise a plurality of specificity domains and/or antigenic domains. Ligand/receptor specificity exchangers having multiple specificity domains and/or antigenic domains are said to be "multimerized" because more than one specificity domain and/or antigenic domain are fused in tandem. Other embodiments concern ligand/receptor specificity exchangers that contain, in addition to a specificity domain and an antigenic domain, sequences that facilitate purification (e.g., a poly histidine tail), linkers (e.g., biotin and/or avidin or streptavidin or the flexible arms of λ phage (λ-linkers)), and sequences or modifications that either promote the stability of the ligand/receptor specificity exchanger (e.g., modifications that provide resistance to protease digestion) or promote the degradation of the ligand/receptor specificity exchanger (e.g., protease cleavage sites). Although the specificity and antigenic domains are preferably peptides, some ligand/receptor specificity exchangers have specificity and antigenic domains that are made of modified or derivatized peptides, peptidomimetics, or chemicals.

The diversity of ligand/receptor specificity exchangers is vast because the embodiments described herein can bind to many different receptors on many different pathogens. Thus, the term "pathogen" is used herein in a general sense to refer to an etiological agent of disease in animals including, but not limited to, bacteria, parasites, fungus, mold, viruses, and cancer cells. Similarly, the term "receptor" is used in a general sense to refer to a molecule (usually a peptide other than a sequence found in an antibody, but can be a carbohydrate, lipid, or nucleic acid) that interacts with a "ligand" (usually a peptide other than a sequence found in an antibody, or a carbohydrate, lipid, nucleic acid or combination thereof). A "receptor", as used herein, does not have to undergo signal transduction and can be involved in a number of molecular interactions including, but not limited to, adhesion (e.g., integrins) and molecular signaling (e.g., growth factor receptors). For example, desired specificity domains comprise a ligand that has a peptide sequence that is present in an extracellular matrix protein (e.g., fibrinogen, collagen, vitronectin, laminin, plasminogen, thrombospondin, and fibronectin) and some specificity domains comprise a ligand that interacts with a bacterial adhesion receptor (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein).

In other embodiments, the specificity domain comprises a ligand that has a peptide sequence that interacts with a viral receptor (e.g., a fragment of T4 glycoprotein that binds gp120 or a fragment of the preS domain, which binds gp170 of the hepadnavirus family). In still other embodiments, the specificity domain comprises a ligand that interacts with a receptor on a cancer cell (e.g., HER-2/neu (C-erbB2)) or an integrin receptor such as a vitronectin receptor, a laminin receptor, a fibronectin receptor, a collagen receptor, a fibrinogen receptor, an $\alpha_4\beta_1$ receptor, an $\alpha_6\beta_1$ receptor, an $\alpha_3\beta_1$ receptor, an $\alpha_5\beta_1$ receptor, and an $\alpha_v\beta_3$ receptor. Preferred embodiments, however, have a specificity domain that comprises at least 8 amino acids of the alpha-chain of fibrinogen and/or the sequence Arginine-Glycine-Aspartic acid (RGD) and the most preferred embodiments have a specificity domain that comprises a sequence selected from the group consisting of SEQ. ID. Nos. 60–105.

Desired antigenic domains have an epitope that is recognized by an antibody that already exists in a subject. For example, many people are immunized against childhood diseases including, but not limited to, small pox, measles, mumps, rubella, and polio. Thus, antibodies to epitopes on these pathogens can be produced by an immunized person. Desirable antigenic domains have an epitope that is found on one of these etiological agents.

Some embodiments have antigenic domains that interact with an antibody that has been administered to the subject. For example, an antibody that interacts with an antigenic domain on a ligand/receptor specificity exchanger can be co-administered with the ligand/receptor specificity exchanger. Further, an antibody that interacts with a ligand/receptor specificity exchanger may not normally exist in a subject but the subject has acquired the antibody by introduction of a biologic material (e.g., serum, blood, or tissue). For example, subjects that undergo blood transfusion acquire numerous antibodies, some of which can interact with an antigenic domain of a ligand/receptor specificity exchanger.

The most desirable antigenic domains comprise an epitope that is recognized by a high titer antibody. By "high titer antibody" is meant an antibody that has high affinity for an antigen (e.g., an epitope on an antigenic domain). For example, in a solid-phase enzyme linked immunosorbent assay (ELISA), a high titer antibody corresponds to an antibody present in a serum sample that remains positive in the assay after a dilution of the serum to approximately the range of 1:100–1:1000 in an appropriate dilution buffer, preferably, about 1:500. The preferred antigenic domains, however, have an epitope found on herpes simplex virus gG2 protein, hepatitis B virus s antigen (HBsAg), hepatitis B virus e antigen (HBeAg), hepatitis B virus c antigen (HBcAg), TT virus, and the poliovirus or combination thereof or comprise a sequence selected from the group consisting of SEQ. ID. Nos. 43–59.

The ligand/receptor specificity exchangers described herein can be made by conventional techniques in recombinant engineering and/or peptide chemistry. In some embodiments, the specificity and antigenic domains are made separately and are subsequently joined together (e.g., through linkers or by association with a common carrier molecule). In other embodiments, the specificity domain and antigenic domain are made as part of the same molecule. By one approach, a ligand/receptor specificity exchanger having a specificity domain joined to an antigenic domain is made by a peptide synthesizer. By another approach, a nucleic acid encoding the specificity domain fused to an antigenic domain is cloned into an expression construct, transfected to cells, and the ligand/receptor specificity exchanger is purified or isolated from the cells or cell supernatent.

Once the ligand/receptor specificity exchanger is made, it can be screened to determine its ability to interact with the receptor on the pathogen and/or an antibody specific for the antigenic domain. Thus, the term "characterization assay" is used to refer to an experiment or evaluation of the ability of a ligand/receptor specificity exchanger to interact with a receptor on a pathogen or cancer cell or fragment thereof and/or an antibody specific for the antigenic domain. Some characterization assays, for example, evaluate the ability of a ligand/receptor specificity exchanger to bind to a support having a receptor of a pathogen or fragment thereof disposed thereon or vice versa. Other characterization assays assess the ability of a ligand/receptor specificity exchanger to bind to an antibody specific for the antigenic domain of the ligand/receptor specificity exchanger. Still other characterization assays evaluate the ability of the ligand/receptor specificity exchanger to effect infection by the pathogen or cancer cell proliferation in cultured cell lines or diseased animals.

The ligand/receptor specificity exchangers described herein can be used as the active ingredients in pharmaceuticals for the treatment and prevention of pathogenic infection, as well as cancer, in animals including humans. The pharmaceutical embodiments can be formulated in many ways and may contain excipients, binders, emulsifiers, carriers, and other auxiliary agents in addition to the ligand/receptor specificity exchanger. Pharmaceuticals comprising a ligand/receptor specificity exchanger can be administered by several routes including, but not limited to, topical, transdermal, parenteral, gastrointestinal, transbronchial, and transalveolar. Ligand/receptor specificity exchangers can also be used as a coating for medical equipment and prosthetics to prevent infection or the spread of disease. The amount of ligand/receptor specificity exchanger provided in a pharmaceutical, therapeutic protocol, or applied to a medical device varies depending on the intended use, the patient, and the frequency of administration.

Some of the methods disclosed concern the administration of a ligand/receptor specificity exchanger to a subject in need of treatment and/or prevention of bacterial infection, fungal infection, viral infection, and cancer. By one approach, a subject suffering from bacterial infection is provided a ligand/receptor specificity exchanger that comprises a specificity domain, which interacts with a bacterial receptor. Similarly, a subject suffering from a viral infection can be provided a ligand/receptor specificity exchanger that comprises a specificity domain that interacts with a viral receptor and a subject suffering from cancer is provided a ligand/receptor specificity exchanger that comprises a specificity domain that interacts with a receptor on the cancer cells. Once a receptor/specificity exchanger complex is formed, it is contemplated that the pathogen or cancer cell is cleared from the body by complement fixation and/or macrophage degradation.

Methods of treatment and prevention of disease (e.g., bacterial, fungal, and viral infection, and cancer) are provided in which a subject suffering from disease or a subject at risk for contracting a disease is identified and then is provided a therapeutically effective amount of a ligand/receptor specificity exchanger that interacts with a receptor present on the etiological agent. Accordingly, subjects suffering from a bacterial infection, fungal infection, viral infection, or cancer are identified by conventional clinical and diagnostic evaluation and are provided a therapeutically effective amount of a ligand/receptor specificity exchanger that interacts with the particular pathogen or cancer cell. Although the ligand/receptor specificity exchangers described herein can be administered to all animals at risk of disease for prophylactic purposes, it may be desired to administer the ligand/receptor specificity exchangers only to those individuals that are in a high risk category (e.g., infants, the elderly, and those that come in close contact with pathogens). As stated above, high risk individuals are identified by currently available clinical and diagnostic techniques.

The section below provides more description of various types of ligand/receptor specificity exchangers that interact with receptors on bacteria, parasites, fungus, mold, viruses, and cancer cells.

Ligand/Receptor Specificity Exchangers that Interact with Receptors on a Pathogen The ligand/receptor specificity exchangers that interact with receptors on a pathogen have a variety of chemical structures but, in a general sense, they are characterized as having at least one region that binds to the receptor (the specificity domain) and at least one region that interacts with an antibody that is specific for an epitope of a pathogen or toxin (the antigenic domain). Preferred ligand/receptor specificity exchangers are peptides but some embodiments comprise derivatized or modified peptides or a peptidomimetic structure. For example, a typical peptide-based ligand/receptor specificity exchanger can be modified to have substituents not normally found on a peptide or to have substituents that are normally found on a peptide but are incorporated at regions that are not normal. In this vein, a peptide-based ligand/receptor specificity exchanger can be acetylated, acylated, or aminated and the substituents that can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. Thus, the term "ligand/receptor specificity exchanger" is a broad one that encompasses modified or unmodified peptide structures, as well as peptidomimetics and chemical structures.

There are many ways to make a peptidomimetic that resembles a peptide-based ligand/receptor specificity exchanger. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a peptide but that avoid the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2$ S] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2$ NH] and hydroxyethylene [$CHOHCH_2$] bioisosteres at the Leu-Val amide bond in the 6–13 octapeptide derived from angiotensinogen, all of which are expressly incorporated by reference in their entireties).

In general, the design and synthesis of a peptidomimetic that resembles a ligand/receptor specificity exchanger involves starting with the sequence of the ligand/receptor specificity exchanger and conformation data (e.g., geometry data, such as bond lengths and angles) of a desired ligand/receptor specificity exchanger (e.g., the most probable simulated peptide), and using such data to determine the geometries that should be designed into the peptidomimetic. Numerous methods and techniques are known in the art for performing this step, any of which could be used. (See, e.g., Farmer, P. S., *Drug Design*, (Ariens, E. J. ed.), Vol. 10, pp. 119–143 (Academic Press, New York, London, Toronto, Sydney and San Francisco) (1980); Farmer, et al., in *TIPS*, 9/82, pp. 362–365; Verber et al., in *TINS*, 9/85, pp. 392–396; Kaltenbronn et al., in *J. Med. Chem.* 33: 838–845 (1990); and Spatola, A. F., in *Chemistry and Biochemistry of Amino Acids. Peptides, and Proteins*, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of β-sheets and α-helices in Peptides," Tibech, Vol. 8, pp. 249–255 (1990), all of which are expressly incorporated by reference in their entireties). Additional teachings can be found in U.S. Pat. Nos. 5,288,707; 5,552,534; 5,811,515; 5,817,626; 5,817,879; 5,821,231; and 5,874,529, all of which are expressly incorporated by reference in their entireties. Once the peptidomimetic is designed, it can be made using conventional techniques in peptide chemistry and/or organic chemistry.

Some embodiments comprise a plurality of specificity domains and/or a plurality of antigenic domains. One type of ligand/receptor specificity exchanger that has a plurality of specificity domains and/or antigenic domains is referred to as a "multimerized ligand/receptor specificity exchanger" because it has multiple specificity domains and/or antigenic domains that appear in tandem on the same molecule. For example, a multimerized specificity domain may have two or more ligands that interact with one type of receptor, two or more ligands that interact with different types of receptors on the pathogen, and two or more ligands that interact with different types of receptors on different pathogens.

Similarly, a multimerized antigenic domain can be constructed to have multimers of the same epitope of a pathogen or different epitopes of a pathogen, which can also be multimerized. That is, some multimerized antigenic domains are multivalent because the same epitope is repeated. In contrast, some multimerized antigenic domains have more than one epitope present on the same molecule in tandem but the epitopes are different. In this respect, these antigenic domains are multimerized but not multivalent. Further, some multimerized antigenic domains are constructed to have different epitopes but the different epitopes are themselves multivalent because each type of epitope is repeated.

Some ligand/receptor specificity exchangers comprise other elements in addition to the specificity domain and antigenic domain such as sequences that facilitate purification, linkers that provide greater flexibility and reduce steric hindrance, and sequences that either provide greater stability to the ligand/receptor specificity exchanger (e.g., resistance to protease degradation) or promote degradation (e.g., protease recognition sites). For example, the ligand/receptor specificity exchangers can comprise cleavable signal sequences that promote cytoplasmic export of the peptide and/or cleavable sequence tags that facilitate purification on antibody columns, glutathione columns, and metal columns.

Ligand/receptor specificity exchangers can comprise elements that promote flexibility of the molecule, reduce steric hindrance, or allow the ligand/receptor specificity exchanger to be attached to a support or other molecule. These elements are collectively referred to as "linkers". One type of linker that can be incorporated with a ligand/receptor specificity exchanger, for example, is avidin or streptavidin (or their ligand-biotin). Through a biotin-avidin/streptavidin linkage, multiple ligand/receptor specificity exchangers can be joined together (e.g., through a support, such as a resin, or directly) or individual specificity domains and antigenic domains can be joined. Another example of a linker that can be included in a ligand/receptor specificity exchanger is referred to as a "λ linker" because it has a sequence that is found on λ phage. Preferred λ sequences are those that correspond to the flexible arms of the phage. These sequences can be included in a ligand/receptor specificity exchanger (e.g., between the specificity domain and the antigenic domain or between multimers of the specificity and/or antigenic domains) so as to provide greater flexibility and reduce steric hindrance.

Additionally, ligand/receptor specificity exchangers can include sequences that either confer resistance to protease degradation or promote protease degradation. By incorporating multiple cysteines in a ligand/receptor specificity exchanger, for example, greater resistance to protease degradation can be obtained. These embodiments of the ligand/receptor specificity exchanger are expected to remain in the body for extended periods, which may be beneficial for some therapeutic applications. In contrast, ligand/receptor specificity exchangers can also include sequences that promote rapid degradation so as to promote rapid clearance from the body. Many sequences that serve as recognition sites for serine, cysteine, and aspartic proteases are known and can be included in a ligand/receptor specificity exchanger. The section below describes the specificity domains in greater detail.

Specificity Domains

The types of specificity domains that can be used with a ligand/receptor specificity exchanger are diverse because a vast number of ligands are known to interact with receptors on bacteria, parasites, fungus, mold, viruses, and cancer cells. Many types of bacteria, parasites, fungus, mold, viruses, and cancer cells, for example, interact with extracellular matrix proteins. Thus, desired specificity domains comprise at least one ligand that has a peptide sequence that is present in an extracellular matrix protein. That is, a specificity domain can have a ligand that has a peptide sequence found in, for example, fibrinogen, collagen, vitronectin, laminin, plasminogen, thrombospondin, and fibronectin.

Investigators have mapped the regions of extracellular matrix proteins that interact with several receptors. (See e.g., McDevvit et al., *Eur. J. Biochem.*, 247:416–424 (1997); Flock, *Molecular Med. Today*, 5:532 (1999); and Pei et al., *Infect. and Immun.* 67:4525 (1999), all of which are herein expressly incorporated by reference in their entirety). Some receptors bind to the same region of the extracellular matrix protein, some have overlapping binding domains, and some bind to different regions altogether. Preferably, the ligands that make up the specificity domain have an amino acid sequence that has been identified as being involved in adhesion to an extracellular matrix protein. It should be understood, however, that random fragments of known ligands for any receptor on a pathogen can be used to generate ligand/receptor specificity exchangers and these candidate ligand/receptor specificity exchangers can be screened in the characterization assays described infra to identify the molecules that interact with the receptors on the pathogen.

Some specificity domains have a ligand that interacts with a bacterial adhesion receptor including, but not limited to, extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein. Ligands that have an amino acid sequence corresponding to the C-terminal portion of the gamma-chain of fibrinogen have been shown to competitively inhibit binding of fibrinogen to ClfA, a *Staphylococcus aureus* adhesion receptor. (McDevvit et al., *Eur. J. Biochem.*, 247:416–424 (1997)). Further, Staphylococcus organisms produce many more adhesion receptors such as Efb, which binds to the alpha chain fibrinogen, ClfB, which interacts with both the α and β chain of fibrinogen, and Fbe, which binds to the β chain of fibrinogen. (Pei et al., *Infect. and Immun.* 67:4525 (1999)). Accordingly, preferred specificity domains comprise at least 3 amino acids of a sequence present in a molecule (e.g., fibrinogen) that can bind to a bacterial adhesion receptor.

Specificity domains can also comprise a ligand that interacts with a viral receptor. Several viral receptors and corresponding ligands are known and these ligands or fragments thereof can be incorporated into a ligand/receptor specificity exchanger. For example, Tong et al., has identified an Hepadnavirus receptor, a 170 kd cell surface glycoprotein that interacts with the pre-S domain of the duck hepatitis B virus envelope protein (U.S. Pat. No. 5,929,220) and Maddon et al., has determined that the T cell surface protein CD4 (or the soluble form termedT4) interacts with gp120 of HIV (U.S. Pat. No. 6,093,539); both references are herein expressly incorporated by reference in their entireties. Thus, specificity domains that interact with a viral receptor can comprise regions of the pre-S domain of the duck hepatitis B virus envelope protein (e.g., amino acid residues 80–102 or 80–104) or regions of the T cell surface protein CD4 (or the soluble form termedT4) that interacts with gp120 of HIV (e.g., the extracellular domain of CD4/T4 or fragments thereof). Many more ligands for viral receptors exist and these molecules or fragments thereof can be used as a specificity domain.

Specificity domains can also comprise a ligand that interacts with a receptor present on a cancer cell. The proto-oncogene HER-2/neu (C-erbB2) encodes a surface growth factor receptor of the tyrosine kinase family, p185HER2. Twenty to thirty percent of breast cancer patients over express the gene encoding HER-2/neu (C-erbB2), via gene amplification. Thus, ligand/receptor specificity exchangers comprising a specificity domain that encodes a ligand for HER-2/neu (C-erbB2) are desirable embodiments. Many types of cancer cells also over express or differentially express integrin receptors. Many preferred embodiments comprise a specificity domain that interacts with an integrin receptor. Although integrins predominantly interact with extracellular matrix proteins, it is known that these receptors interact with other ligands such as invasins, RGD-containing peptides (i.e., Arginine-Glycine-Aspartate), and chemicals. (See e.g., U.S. Pat. Nos. 6,090,944 and 6,090,388; and Brett et al., *Eur J Immunol*, 23:1608 (1993), all of which are hereby expressly incorporated by reference in their entireties). Ligands for integrin receptors include, but are not limited to, molecules that interact with a vitronectin receptor, a laminin receptor, a fibronectin receptor, a collagen receptor, a fibrinogen receptor, an $\alpha_4\beta_1$ receptor, an $\alpha_6\beta_1$ receptor, an $\alpha_3\beta_1$ receptor, an $\alpha_5\beta_1$ receptor, and an $\alpha_v\beta_3$ receptor. TABLE I also lists several preferred specificity domains. The specificity domains described above are provided for illustrative purposes only and in no way should be construed to limit the scope of specificity domains that can be used with the embodiments described herein. The next section describes antigenic domains in greater detail.

TABLE I

| SPECIFICITY DOMAINS | |
|---|---|
| YGEGQQHHLGGAKQAGDV | (SEQ. ID. No. 1) |
| MSWSLHPRNLILYFYALLFL | (SEQ. ID. No. 2) |
| ILYFYALLFLSTCVAYVAT | (SEQ. ID. No. 3) |
| SSTCVAYVATRDNCCILDER | (SEQ. ID. No. 4) |
| RDNCCILDERFGSYCPTTCG | (SEQ. ID. No. 5) |
| FGSYCPTTCGIADFLSTYQT | (SEQ. ID. No. 6) |
| IADFLSTYQTKVDKDLQSLE | (SEQ. ID. No. 7) |
| KVDKDLQSLEDILHQVENKT | (SEQ. ID. No. 8) |
| DILHQVENKTSEVKQLIKAI | (SEQ. ID. No. 9) |
| SEVKQLIKAIQLTYNPDESS | (SEQ. ID. No. 10) |
| QLTYNPDESSKPNMIDAATL | (SEQ. ID. No. 11) |
| KPNMIDAATLKSRIMLEEIM | (SEQ. ID. No. 12) |
| KSRIMLEEIMKYEASILTHD | (SEQ. ID. No. 13) |
| KYEASILTHDSSIRYLQEIY | (SEQ. ID. No. 14) |
| SSIRYLQEIYNSNNQKIVNL | (SEQ. ID. No. 15) |
| NSNNQKIVNLKEKVAQLEAQ | (SEQ. ID. No. 16) |
| CQEPCKDTVQIHDITGKDCQ | (SEQ. ID. No. 17) |
| IHDITGKDCQDIANKGAKQS | (SEQ. ID. No. 18) |
| DIANKGAKQSGLYFIKPLKA | (SEQ. ID. No. 19) |
| GLYFIKPLKANQQFLVYCEI | (SEQ. ID. No. 20) |
| NQQFLVYCEIDGSGNGWTVF | (SEQ. ID. No. 21) |
| DGSGNGWTVFQKRLDGSVDF | (SEQ. ID. No. 22) |
| QKRLDGSVDFKKNWIQYKEG | (SEQ. ID. No. 23) |
| KKNWIQYKEGFGHLSPTGTT | (SEQ. ID. No. 24) |
| FGHLSPTGTTEFWLGNEKIH | (SEQ. ID. No. 25) |
| EFWLGNEKIHLISTQSAIPY | (SEQ. ID. No. 26) |
| LISTQSAIPYALRVELEDWN | (SEQ. ID. No. 27) |
| ALRVELEDWNGRTSTADYAM | (SEQ. ID. No. 28) |
| GRTSTADYAMFKVGPEADKY | (SEQ. ID. No. 29) |
| FKVGPEADKYRLTYAYFAGG | (SEQ. ID. No. 30) |
| RLTYAYFAGGDAGDAFDGFD | (SEQ. ID. No. 31) |
| DAGDAFDGFDFGDDPSDKFF | (SEQ. ID. No. 32) |
| FGDDPSDKFFTSHNGMQFST | (SEQ. ID. No. 33) |
| TSHNGMQFSTWDNDNDKFEG | (SEQ. ID. No. 34) |
| WDNDNDKFEGNCAEQDGSGW | (SEQ. ID. No. 35) |
| NCAEQDGSGWWMNKCHAGHL | (SEQ. ID. No. 36) |

TABLE I-continued

| SPECIFICITY DOMAINS | |
|---|---|
| WMNKCHAGHLNGVYYQGGTY | (SEQ. ID. No. 37) |
| NGVYYQGGTYSKASTPNGYD | (SEQ. ID. No. 38) |
| SKASTPNGYDNGIIWATWKT | (SEQ. ID. No. 39) |
| NGIIWATWKTRWYSMKKTTM | (SEQ. ID. No. 40) |
| RWYSMKKTTMKIIPFNRLTI | (SEQ. ID. No. 41) |
| KIIPFNRLTIGEGQQHHLGGAKQAGDV | (SEQ. ID. No. 42) |

Antigenic Domains

The diversity of antigenic domains that can be used in the ligand/receptor specificity exchangers is also quite large because a pathogen or toxin can present many different epitopes. That is, the antigenic domains that can be incorporated into a ligand/receptor specificity exchanger include epitopes presented by bacteria, fungus, plants, mold, virus, cancer cells, and toxins. Desired antigenic domains comprise an epitope of a pathogen that already exists in a subject by virtue of naturally acquired immunity or vaccination. Epitopes of pathogens that cause childhood diseases, for example, can be used as antigenic domains.

Some embodiments have antigenic domains that interact with an antibody that has been administered to the subject. For example, an antibody that interacts with an antigenic domain on a specificity exchanger can be co-administered with the specificity exchanger. Further, an antibody that interacts with a ligand/receptor specificity exchanger may not normally exist in a subject but the subject has acquired the antibody by introduction of a biologic material (e.g., serum, blood, or tissue). For example, subjects that undergo blood transfusion acquire numerous antibodies, some of which can interact with an antigenic domain of a ligand/receptor specificity exchanger. Some preferred antigenic domains for use in a ligand/receptor specificity exchanger comprise viral epitopes including, but not limited to, the herpes simplex virus, hepatitis B virus, TT virus, and the poliovirus.

In some embodiments, it is also preferred that the antigenic domains comprise an epitope of a pathogen or toxin that is recognized by a "high-titer antibody". Approaches to determine whether the epitope of a pathogen or toxin is recognizable by a high titer antibody are provided infra. Epitopes of a pathogen that can be included in an antigenic domain of a ligand/receptor specificity exchanger include epitopes on peptide sequences disclosed in Swedish Pat No. 9901601-6; U.S. Pat. No. 5,869,232; *Mol. Immunol.* 28: 719–726 (1991); and *J. Med. Virol.* 33:248–252 (1991); all references are herein expressly incorporated by reference in their entireties. TABLE II provides the amino acid sequence of several preferred antigenic domains.

The section following TABLE II, describes the preparation of ligand/receptor specificity exchangers in greater detail.

TABLE II

| ANTIGENIC DOMAINS | |
|---|---|
| GLYSSIWLSPGRSYFET | (SEQ. ID. No. 43) |
| YTDIKYNPFTDRGEGNM | (SEQ. ID. No. 44) |
| DQNIHMNARLLIRSPFT | (SEQ. ID. No. 45) |
| LIRSPFTDPQLLVHTDP | (SEQ. ID. No. 46) |
| QKESLLFPPVKLLRRVP | (SEQ. ID. No. 47) |
| PALTAVETGAT | (SEQ. ID. No. 48) |
| STLVPETT | (SEQ. ID. No. 49) |

TABLE II-continued

| ANTIGENIC DOMAINS | |
|---|---|
| TPPAYRPPNAPIIL | (SEQ. ID. No. 50) |
| EIPALTAVE | (SEQ. ID. No. 51) |
| LEDPASRDLV | (SEQ. ID. No. 52) |
| HRGGPEEF | (SEQ. ID. No. 53) |
| HRGGPEE | (SEQ. ID. No. 54) |
| VLICGENTVSRNYATHS | (SEQ. ID. No. 55) |
| KINTMPPFLDTELTAPS | (SEQ. ID. No. 56) |
| PDEKSQREILLNKIASY | (SEQ. ID. No. 57) |
| TATTTTYAYPGTNRPPV | (SEQ. ID. No. 58) |
| STPLPETT | (SEQ. ID. No. 59) |

Methods of Making Ligand/Receptor Specificity Exchangers that Interact with Receptors on Bacteria, Parasites, Fungus, Mold, Viruses, and Cancer Cells In some embodiments, the specificity and antigenic domains are made separately and are subsequently joined together (e.g., through linkers or by association with a common carrier molecule) and in other embodiments, the specificity domain and antigenic domain are made as part of the same molecule. For example, any of the specificity domains listed in TABLE I can be joined to any of the antigenic domains of TABLE II. Although the specificity and antigenic domains could be made separately and joined together through a linker or carrier molecule (e.g., a complex comprising a biotinylated specificity domain, streptavidin, and a biotinylated antigenic domain), it is preferred that the ligand/receptor specificity exchanger is made as a fusion protein. Thus, preferred embodiments include fusion proteins comprising any of the specificity domains listed in TABLE I joined to any of the antigenic domains of TABLE II.

Ligand/receptor specificity exchangers can be generated in accordance with conventional methods of protein engineering, protein chemistry, organic chemistry, and molecular biology. Additionally, some commercial enterprises manufacture made-to-order peptides and a ligand/receptor specificity exchanger can be obtained by providing such a company with the sequence of a desired ligand/receptor specificity exchanger and employing their service to manufacture the agent according to particular specifications (e.g., Bachem AG, Switzerland). Preferably, the ligand/receptor specificity exchangers are prepared by chemical synthesis methods (such as solid phase peptide synthesis) using techniques known in the art, such as those set forth by Merrifield et al., *J. Am. Chem. Soc.* 85:2149 (1964), Houghten et al., *Proc. Natl. Acad. Sci. USA*, 82:51:32 (1985), Stewart and Young (*Solid phase peptide synthesis*, Pierce Chem Co., Rockford, Ill. (1984), and Creighton, 1983, *Proteins: Structures and Molecular Principles*, W. H. Freeman & Co., N.Y.; all references are herein expressly incorporated by reference in their entireties.

By one approach, solid phase peptide synthesis is performed using an Applied Biosystems 430A peptide synthesizer (Applied Biosystems, Foster City, Calif.). Each synthesis uses a p-methylbenzylhydrylamine solid phase support resin (Peptide International, Louisville, Ky.) yielding a carboxyl terminal amide when the peptides are cleaved off from the solid support by acid hydrolysis. Prior to use, the carboxyl terminal amide can be removed and the ligand/receptor specificity exchangers can be purified by high performance liquid chromatography (e.g., reverse phase high performance liquid chromatography (RP-HPLC) using a PepS-15 C18 column (Pharmacia, Uppsala, Sweden)) and sequenced on an Applied Biosystems 473A peptide sequencer. An alternative synthetic approach uses an automated peptide synthesizer (Syro, Multisyntech, Tubingen, Germany) and 9-fluorenylmethoxycarbonyl (finoc) protected amino acids (Milligen, Bedford, Mass.).

While the ligand/receptor specificity exchangers can be chemically synthesized, it can be more efficient to produce these polypeptides by recombinant DNA technology using techniques well known in the art. Such methods can be used to construct expression vectors containing nucleotide sequences encoding a ligand/receptor specificity exchanger and appropriate transcriptional and translational control signals. These methods include, for example, in vitro recombinant DNA techniques, synthetic techniques, and in vivo genetic recombination. Alternatively, RNA capable of encoding a ligand/receptor specificity exchanger can be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems can be utilized to express the ligand/receptor specificity exchangers. Where the ligand/receptor specificity exchanger is a soluble molecule it can be recovered from the culture, i.e., from the host cell in cases where the peptide or polypeptide is not secreted, and from the culture media in cases where the peptide or polypeptide is secreted by the cells. However, the expression systems also encompass engineered host cells that express membrane bound ligand/receptor specificity exchangers. Purification or enrichment of the ligand/receptor specificity exchangers from such expression systems can be accomplished using appropriate detergents and lipid micelles and methods well known to those skilled in the art.

The expression systems that can be used include, but are not limited to, microorganisms such as bacteria (e.g., *E. coli* or *B. subtilis*) transformed with recombinant bacteriophage DNA, plasmid DNA or cosmid DNA expression vectors containing nucleotide sequences encoding a ligand/receptor specificity exchanger; yeast (e.g., Saccharomyces, Pichia) transformed with recombinant yeast expression vectors containing nucleotide sequences encoding ligand/receptor specificity exchangers; insect cell systems infected with recombinant virus expression vectors (e.g., Baculovirus) containing nucleic acids encoding the ligand/receptor specificity exchangers; or mammalian cell systems (e.g., COS, CHO, BHK, 293, 3T3) harboring recombinant expression constructs containing nucleic acids encoding ligand/receptor specificity exchangers.

In bacterial systems, a number of expression vectors can be advantageously selected depending upon the use intended for the ligand/receptor specificity exchanger. For example, when a large quantity is desired (e.g., for the generation of pharmaceutical compositions of ligand/receptor specificity exchangers) vectors that direct the expression of high levels of fusion protein products that are readily purified can be desirable. Such vectors include, but are not limited, to the *E. coli* expression vector pUR278 (Ruther et al., *EMBO J.*, 2:1791 (1983), in which the ligand/receptor specificity exchanger coding sequence can be ligated individually into the vector in frame with the lacZ coding region so that a fusion protein is produced; pIN vectors (Inouye & Inouye, *Nucleic Acids Res.*, 13:3101–3109 (1985); Van Heeke & Schuster, *J. Biol. Chem.*, 264:5503–5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The ligand/receptor specificity exchanger gene coding sequence can be cloned individually into non-essential regions (for example the polyhedrin gene) of the virus and placed under control of an AcNPV promoter (for example the polyhedrin promoter). Successful insertion of ligand/receptor specificity exchanger gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., *J. Virol.* 46: 584 (1983); and Smith, U.S. Pat. No. 4,215,051).

In mammalian host cells, a number of viral-based expression systems can be utilized. In cases where an adenovirus is used as an expression vector, a nucleic acid sequence encoding a ligand/receptor specificity exchanger can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the ligand/receptor specificity exchanger gene product in infected hosts. (See e.g., Logan & Shenk, *Proc. Natl. Acad. Sci. USA* 81:3655–3659 (1984)). Specific initiation signals can also be required for efficient translation of inserted ligand/receptor specificity exchanger nucleotide sequences (e.g., the ATG initiation codon and adjacent sequences). In most cases, an exogenous translational control signal, including, perhaps, the ATG initiation codon, should be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can also be enhanced by the inclusion of appropriate transcription enhancer elements, transcription terminators, etc. (See Bittner et al., *Methods in Enzymol.*, 153:516–544 (1987)).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for some embodiments. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and W138.

For long-term, high-yield production of recombinant proteins, stable expression is preferred. For example, cell lines that stably express the ligand/receptor specificity exchangers described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express a ligand/receptor specificity exchanger.

A number of selection systems can be used, including but not limited to the herpes simplex virus thymidine kinase (Wigler, et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy, et al., *Cell* 22:817 (1980)) genes can be employed in tk.sup.-, hgprt.sup.- or aprt.sup.- cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980)); O'Hare, et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin, et al., *J. Mol. Biol.* 150:1 (1981)); and hygro, which confers resistance to hygromycin (Santerre, et al., *Gene* 30:147 (1984)). The following section describes the ligand/receptor specificity exchanger characterization assays in greater detail.

Ligand/Receptor Specificity Exchanger Characterization Assays

Preferably, ligand/receptor specificity exchangers are analyzed for their ability to interact with a receptor and/or the ability to interact with an antibody that may be present in a subject. The term "characterization assay" refers to an assay, experiment, or analysis made on a ligand/receptor specificity exchanger, which evaluates the ability of a ligand/receptor specificity exchanger to interact with a receptor (e.g., a surface receptor present in bacteria, virus, mold, or fungi) or an antibody (e.g., an antibody that recognizes an epitope found on a pathogen), or effect the proliferation of a pathogen. Encompassed by the term "characterization assay" are binding studies (e.g., enzyme immunoassays (EIA), enzyme-linked immunoassays (ELISA), competitive binding assays, computer generated binding assays, support bound binding studies, and one and two hybrid systems), and infectivity studies (e.g., reduction of viral infection, propagation, and attachment to a host cell).

Preferred binding assays use multimeric agents. One form of multimeric agent concerns a composition comprising a ligand/receptor specificity exchanger, or fragments thereof disposed on a support. Another form of multimeric agent involves a composition comprising a receptor or an antibody specific for the antigenic domain of a ligand/receptor specificity exchanger disposed on a support. A "support" can be a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. A ligand/receptor specificity exchanger can also be joined to inorganic supports, such as silicon oxide material (e.g. silica gel, zeolite, diatomaceous earth or aminated glass) by, for example, a covalent linkage through a hydroxy, carboxy, or amino group and a reactive group on the support.

In some multimeric agents, the macromolecular support has a hydrophobic surface that interacts with a portion of the ligand/receptor specificity exchanger, receptor or ligand by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, a ligand/receptor specificity exchanger, receptor or an antibody specific for the antigenic domain of a ligand/receptor specificity exchanger can be covalently bound to supports including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the ligand/receptor specificity exchanger, receptor, or antibody specific for the antigenic domain of a ligand/receptor specificity exchanger. For example, cyanogen bromide activated matrices, epoxy activated matrices, thio and thiopropyl gels, nitrophenyl chloroformate and N-hydroxy succinimide chlorformate linkages, or oxirane acrylic supports can be used. (Sigma). Furthermore, in some embodiments, a liposome or lipid bilayer (natural or synthetic) is contemplated as a support and a ligand/receptor specificity exchanger, receptor, or an antibody specific for the antigenic domain of a ligand/receptor specificity exchanger can be attached to the membrane surface or are incorporated into the membrane by techniques in liposome engineering. By one approach, liposome multimeric supports comprise a ligand/receptor specificity exchanger, receptor, or an antibody specific for the antigenic domain of a ligand/receptor specificity exchanger that is exposed on the surface.

The insertion of linkers (e.g., "λ linkers" engineered to resemble the flexible regions of λ phage) of an appropriate length between the ligand/receptor specificity exchanger, receptor, or antibody specific for the antigenic domain of a ligand/receptor specificity exchanger and the support are also contemplated so as to encourage greater flexibility and overcome any steric hindrance that can be presented by the support. The determination of an appropriate length of linker that allows for optimal binding can be found by screening the attached molecule with varying linkers in the characterization assays detailed herein.

Several approaches to characterize ligand/receptor specificity exchangers employ a multimeric described above. For example, support-bound ligand/receptor specificity exchanger can be contacted with "free" adhesion receptors and an association can be determined directly (e.g., by using labeled adhesion receptors) or indirectly (e.g., by using a labeled ligand directed to an adhesion receptor). Thus, candidate ligand/receptor specificity exchangers are identified as bona fide ligand/receptor specificity exchangers by virtue of the association of the receptors with the support-bound candidate ligand/receptor specificity exchanger. Alternatively, support-bound adhesion receptors can be contacted with "free" ligand/receptor specificity exchangers and the amount of associated ligand/receptor specificity exchanger can be determined directly (e.g., by using labeled ligand/receptor specificity exchanger) or indirectly (e.g., by using a labeled antibody directed to the antigenic domain of the ligand/receptor specificity exchanger). Similarly, by using an antibody specific for the antigenic domain of a ligand/receptor specificity exchanger disposed on a support and labeled ligand/receptor specificity exchanger (or a secondary detection reagent, e.g., a labeled receptor or antibody to the ligand/receptor specificity exchanger) the ability of the antibody to bind to the antigenic domain of the ligand/receptor specificity exchanger can be determined.

Some characterization assays evaluate the ability of the ligand/receptor specificity exchanger to interact with the target receptor and the redirecting antibody while other characterization assays are designed to determine whether a ligand/receptor specificity exchanger can bind to both the target receptor and the redirecting antibody. In general, the characterization assays can be classified as: (1) in vitro characterization assays, (2) cellular characterization assays, and (3) in vivo characterization assays. A discussion of each type of characterization assay is provided in the following sections.

In Vitro Characterization Assays

There are many types of in vitro assays that can be used to determine whether a ligand/receptor specificity exchanger binds to a particular receptor and whether an antibody found in a subject can bind to the ligand/receptor specificity exchanger. Most simply, the receptor is bound to a support (e.g., a petri dish) and the association of the ligand/receptor specificity exchanger with the receptor is monitored directly or indirectly, as described above. Similarly, a primary antibody directed to the antigenic domain of a ligand/receptor specificity exchanger (e.g., an antibody found in a subject) can be bound to a support and the association of a ligand/receptor specificity exchanger with the primary antibody can be determined directly (e.g., using labeled ligand/receptor specificity exchanger) or indirectly (e.g., using labeled receptor or a labeled secondary antibody that interacts with an epitope on the ligand/receptor specificity exchanger that does not compete with the epitope recognized by the primary antibody).

Another approach involves a sandwich-type assay, wherein the receptor is bound to a support, the ligand/receptor specificity exchanger is bound to the receptor, and the primary antibody is bound to the ligand/receptor specificity exchanger. If labeled primary antibody is used, the presence of a receptor/specificity exchanger/primary antibody complex can be directly determined. The presence of the receptor/specificity exchanger/primary antibody complex can also be determined indirectly by using, for example, a labeled secondary antibody that reacts with the primary antibody at an epitope that does not interfere with the binding of the primary antibody to the ligand/receptor specificity exchanger. In some cases, it may be desired to use a labeled tertiary antibody to react with an unlabeled secondary antibody, thus, forming a receptor/specificity exchanger/primary antibody/secondary antibody/labeled tertiary antibody complex. The example below describes a characterization assay that was performed to determine whether a ligand/receptor specificity exchanger interacts with bacteria having the ClfA receptor.

EXAMPLE 1

Ligand/receptor specificity exchangers having specificity domains (approximately 20 amino acids long) corresponding to various regions of the fibrinogen gamma-chain sequence were produced using standard techniques in peptide synthesis using finoc chemistry (Syro, MultiSynTech, Germany) and these ligand/receptor specificity exchangers were analyzed for their ability to bind the ClfA receptor and an antibody specific for their antigenic domains. The sequences of these ligand/receptor specificity exchangers are listed in TABLE III and are provided in the Sequence listing (SEQ. ID. Nos. 60–103). The ligand/receptor specificity exchangers used in this analysis have an antigenic domain that presents an epitope of herpes simplex virus gG2 protein, which is recognized by a monoclonal antibody for herpes simplex virus gG2 proteins. Serial dilutions of these ligand/receptor specificity exchangers were made in phosphate buffered saline (PBS) containing 2 μg/ml goat serum. (Sigma Chemicals, St. Louis, Mo.) and 0.5% Tween 20 (PBS-GT). The receptor ClfA was passively adsorbed at 10 μg/ml to 96 well microtiter plates in 50 mM sodium carbonate buffer, pH 9.6, overnight at +4° C.

The diluted ligand/receptor specificity exchangers were then incubated on the plates for 60 minutes. The ability of the ligand/receptor specificity exchanger to interact with the receptor was determined by applying a primary antibody to the plate and incubating for 60 minutes (a 1:1000 dilution of mAb for herpes simplex virus gG2 proteins). The bound primary mAb was then indicated by a rabbit anti-mouse IgG (Sigma) secondary antibody and a peroxidase labeled goat anti-rabbit IgG (Sigma) tertiary antibody. The plates were developed by incubation with dinitro-phenylene-diamine (Sigma) and the absorbance at 405 nm was analyzed.

Every ligand/receptor specificity exchanger provided in TABLE III (SEQ. ID Nos. 60–103) appreciably bound the immobilized ClfA and also allowed for the binding of the mAb specific for HSV gG2 protein. The method described above for determining the affinity of a ligand/receptor specificity exchanger for an adhesion receptor and a primary antibody can be performed for any candidate ligand/receptor specificity exchanger comprising any specificity domain and any antigenic domain provided that the appropriate sequences and adhesion receptors are used.

The example following TABLE III describes several cellular-based characterization assays that can be performed to determine whether a ligand/receptor specificity exchanger has an effect on the proliferation of a pathogen.

TABLE III

| LIGAND/RECEPTOR SPECIFICITY EXCHANGERS | |
|---|---|
| YGEGQQHHLGGAKQAGDV HRGGPEEF | (SEQ. ID. No. 60) |
| YGEGQQHHLGGAKQAGDVHRGGPEE | (SEQ. ID. No. 61) |
| YGEGQQHHLGGAKQAGDVSTPLPETT | (SEQ. ID. No. 62) |
| MSWSLHPRNLILYFYALLFLHRGGPEE | (SEQ. ID. No. 63) |
| ILYFYALLFLSTCVAYVATHRGGPEE | (SEQ. ID. No. 64) |
| SSTCVAYVATRDNCCILDERHRGGPEE | (SEQ. ID. No. 65) |
| RDNCCILDERFGSYCPTTCGHRGGPEE | (SEQ. ID. No. 66) |

TABLE III-continued

| LIGAND/RECEPTOR SPECIFICITY EXCHANGERS | |
|---|---|
| FGSYCPTTCGIADFLSTYQTHRGGPEE | (SEQ. ID. No. 67) |
| IADFLSTYQTKVDKDLQSLEHRGGPEE | (SEQ. ID. No. 68) |
| KVDKDLQSLEDILHQVENKTHRGGPEE | (SEQ. ID. No. 69) |
| DILHQVENKTSEVKQLIKAIHRGGPEE | (SEQ. ID. No. 70) |
| SEVKQLIKAIQLTYNPDESSHRGGPEE | (SEQ. ID. No. 71) |
| QLTYNPDESSKPNMIDAATLHRGGPEE | (SEQ. ID. No. 72) |
| KPNMIDAATLKSRIMLEEIMHRGGPEE | (SEQ. ID. No. 73) |
| KSRIMLEEIMKYEASILTHDHRGGPEE | (SEQ. ID. No. 74) |
| KYEASILTHDSSIRYLQEIYHRGGPEE | (SEQ. ID. No. 75) |
| SSIRYLQEIYNSNNQKIVNLHRGGPEE | (SEQ. ID. No. 76) |
| NSNNQKIVNLKEKVAQLEAQHRGGPEE | (SEQ. ID. No. 77) |
| CQEPCKDTVQIHDITGKDCQHRGGPEE | (SEQ. ID. No. 78) |
| IHDITGKDCQDIANKGAKQSHRGGPEE | (SEQ. ID. No. 79) |
| DIANKGAKQSGLYFIKPLKAHRGGPEE | (SEQ. ID. No. 80) |
| GLYFIKPLKANQQFLVYCEIHRGGPEE | (SEQ. ID. No. 81) |
| NQQFLVYCEIDGSGNGWTVFHRGGPEE | (SEQ. ID. No. 82) |
| DGSGNGWTVFQKRLDGSVDFHRGGPEE | (SEQ. ID. No. 83) |
| QKRLDGSVDFKKNWIQYKEGHRGGPEE | (SEQ. ID. No. 84) |
| KKNWIQYKEGFGHLSPTGTTHRGGPEE | (SEQ. ID. No. 85) |
| FGHLSPTGTTEFWLGNEKIHHRGGPEE | (SEQ. ID. No. 86) |
| EFWLGNEKIHLISTQSAIPYHRGGPEE | (SEQ. ID. No. 87) |
| LISTQSAIPYALRVELEDWNHRGGPEE | (SEQ. ID. No. 88) |
| ALRVELEDWNGRTSTADYAMHRGGPEE | (SEQ. ID. No. 89) |
| GRTSTADYAMFKVGPEADKYHRGGPEE | (SEQ. ID. No. 90) |
| FKVGPEADKYRLTYAYFAGGHRGGPEE | (SEQ. ID. No. 91) |
| RLTYAYFAGGDAGDAFDGFDHRGGPEE | (SEQ. ID. No. 92) |
| DAGDAFDGFDFGDDPSDKFFHRGGPEE | (SEQ. ID. No. 93) |
| FGDDPSDKFFTSHNGMQFSTHRGGPEE | (SEQ. ID. No. 94) |
| TSHNGMQFSTWDNDNDKFEGHRGGPEE | (SEQ. ID. No. 95) |
| WDNDNDKFEGNCAEQDGSGWHRGGPEE | (SEQ. ID. No. 96) |
| NCAEQDGSGWWMNKCHAGHLHRGGPEE | (SEQ. ID. No. 97) |
| WMNKCHAGHLNGVYYQGGTYHRGGPEE | (SEQ. ID. No. 98) |
| NGVYYQGGTYSKASTPNGYDHRGGPEE | (SEQ. ID. No. 99) |
| SKASTPNGYDNGIIWATWKTHRGGPEE | (SEQ. ID. No. 100) |
| NGIIWATWKTRWYSMKKTTMHRGGPEE | (SEQ. ID. No. 101) |
| RWYSMKKTTMKIIPFNRLTIHRGGPEE | (SEQ. ID. No. 102) |
| KIIPFNRLTIGEGQQHHLGGAKQAGDVHRGGPEE | (SEQ. ID. No. 103) |

Pathogen-based Characterization Assays

In another type of characterization assay, a pathogen-based approach is used to evaluate the ability of a ligand/receptor specificity exchanger to interact with a pathogen and an antibody directed to the antigenic domain of the ligand/receptor specificity exchanger. This analysis also reveals the ability of the ligand/receptor specificity exchanger to effect proliferation of a pathogen because, in the body of a subject, the interaction of the ligand/receptor specificity exchanger with a pathogen and an antibody directed to the antigenic domain of the ligand/receptor specificity exchanger is followed by humoral and cellular responses that purge the pathogen from the subject (e.g., complement fixation and macrophage degradation). In general, the pathogen-based characterization assays involve providing ligand/receptor specificity exchangers to cultured pathogens and monitoring the association of the ligand/receptor specificity exchanger with the cells or virus. Several types of pathogen-based characterization assays can be used and the example below describes some of the preferred characterization assays in greater detail.

EXAMPLE 2

One type of pathogen-based characterization assay involves binding of a ligand/receptor specificity exchanger to bacteria disposed on a support. Accordingly, bacteria that produce Clfa (e.g., *Staphylococcus aureus*, or *Escherichia coli.*) are grown in culture or on a agar plate in a suitable growth media (e.g., LB broth, blood broth, LB agar or blood agar). The cells are then transferred to a membrane (e.g., nitrocellulose or nylon) by either placing the culture on the membrane under vacuum (e.g., using a dot-blot manifold apparatus) or by placing the membrane on the colonies for a time sufficient to permit transfer. The cells that are bound to the membrane are then provided a serial dilution of a ligand/receptor specificity exchanger (e.g., 500 ng, 1 μg, 5 μg, 10 μg, 25 μg, and 50 μg of ligand/receptor specificity exchanger in a total volume of 200 μl of PBS). In one experiment, the ligand/receptor specificity exchangers listed in TABLE III are used. The diluted ligand/receptor specificity exchangers are then incubated on the membranes for 60 minutes. Subsequently, the non-bound ligand/receptor specificity exchangers are removed and the membrane is washed with PBS (e.g., 3 washes with 2 ml of PBS per wash). Next, a 1:100–1:1000 dilution of a primary antibody that interacts with the antigenic domain of the ligand/receptor specificity exchanger (e.g., mAb for herpes simplex virus gG2 protein) is provided and the binding reaction is allowed to occur for 60 minutes. Again, the membrane is washed with PBS (e.g., 3 washes with 2 ml of PBS per wash) to remove unbound primary antibody. Appropriate controls include the membrane itself, bacteria on the membrane without a ligand/receptor specificity exchanger, and bacteria on the membrane with ligand/receptor specificity exchanger but no primary antibody.

To detect the amount of ligand/receptor specificity exchanger bound to the bacteria on the membrane, a secondary antibody (e.g., rabbit anti-mouse IgG (Sigma)) and a tertiary antibody (e.g., a peroxidase labeled goat anti-rabbit IgG (Sigma)) are used. Of course, a labeled secondary antibody that interacts with the primary antibody can be used as well. As above, the secondary antibody is contacted with the membrane for 60 minutes and the non-bound secondary antibody is washed from the membrane with PBS (e.g., 3 washes with 2 ml of PBS per wash). Then, the tertiary antibody is contacted with the membrane for 60 minutes and the non-bound tertiary antibody is washed from the membrane with PBS (e.g., 3 washes with 2 ml of PBS per wash). The bound tertiary antibody can be detected by incubating the membrane with dinitro-phenylene-diamine (Sigma).

Another approach involves the use of an immobilized ligand/receptor specificity exchanger. Accordingly, primary antibody (e.g., mAb for herpes simplex virus gG2 protein) is bound to a petri dish. Once the primary antibody is bound, various dilutions of a ligand/receptor specificity exchanger (e.g., a ligand/receptor specificity exchanger provided in TABLE III) are added to the coated dish. The ligand/receptor specificity exchanger is allowed to associate with the primary antibody for 60 minutes and the non-bound ligand/receptor specificity exchanger is washed away (e.g., three washes with 2 ml of PBS). Appropriate controls include petri dishes without primary antibody or ligand/receptor specificity exchanger.

Subsequently, a turbid solution of bacteria (e.g., *E. coli*) are added to the petri dishes and the bacteria are allowed to interact with the immobilized ligand/receptor specificity exchanger for 60 minutes. The non-bound bacteria are then removed by washing with PBS (e.g., 3 washes with 2 ml of PBS). Next, growth media (e.g., LB broth) is added to the petri dish and the culture is incubated overnight. Alternatively, LB agar is added to the petri dish and the culture is incubated overnight. An interaction between the ligand/receptor specificity exchanger and the bacteria can be observed visually (e.g., turbid growth media, which can be quantified using spectrophotometric analysis or the appearance of colonies on the agar).

By modifying the approaches described above, one of skill in the art can evaluate the ability of a ligand/receptor specificity exchanger to interact with a virus. For example, soluble fragments of T4 glycoprotein have been shown to interact with a human immunodeficiency virus (HIV) envelope glycoprotein. (See e.g., U.S. Pat. No. 6,093,539, herein expressly incorporated by reference in its entirety). Ligand/receptor specificity exchangers having a specificity domain comprising a fragment of T4 glycoprotein that interacts with HIV envelope glycoprotein (e.g., amino acids 1–419 of the T4 glycoprotein sequence provided in U.S. Pat. No. 6,093,539 or a portion thereof) can be made by synthesizing a fusion protein having the specificity domain joined to an antigenic domain (e.g., an antigenic domain listed in TABLE II). Although peptide chemistry can be used to make the ligand/receptor specificity exchanger, it is preferred that an expression construct having the fragment of T4 glycoprotein joined to an antigenic domain is made and transfected into a suitable cell. The expression and purification strategies described in U.S. Pat. No. 6,093,539 and above can also be employed.

Once the ligand/receptor specificity exchanger has been constructed a filter binding assay is performed. Accordingly, serial ten-fold dilutions of HIV inoculum are applied to a membrane (e.g. nitrocellulose or nylon) in a dot blot apparatus under constant vacuum. Then serial ten fold dilutions of the ligand/receptor specificity exchanger are applied to the bound HIV particles. The ligand/receptor specificity exchanger is contacted with the particles for 60 minutes before applying vacuum and washing with PBS (e.g., 3 washes with 2 ml of PBS per wash)). Once the non-bound ligand/receptor specificity exchanger is removed, ten fold serial dilutions of the primary antibody, which binds to the antigenic domain, are added to the samples and the binding reaction is allowed to occur for 60 minutes. Then a vacuum is applied and the non-bound primary antibody is washed with PBS (e.g., 3 washes with 2 ml of PBS per wash)). The detection of the bound primary antibody can be accomplished, as described above.

The ability of a ligand/receptor specificity exchanger to interact with a virus can also be evaluated in a sandwich-type assay. Accordingly, a primary antibody that interacts with the antigenic domain of the ligand/receptor specificity exchanger is immobilized in micro titer wells and serial dilutions of ligand/receptor specificity exchanger are added to the primary antibody so as to create a primary antibody/specificity exchanger complex, as described above. Next, ten fold serial dilutions of HIV inoculum are added and the binding reaction is allowed to occur for 60 minutes. Non-bound HIV particles are removed by successive washes in PBS. Detection of the bound HIV particles can be accomplished using a radiolabeled anti-HIV antibody (e.g., antibody obtained from sera from a person suffering with HIV infection).

While the examples above describe pathogen-based assays using bacteria and a virus, modifications of these approaches can be made to study the interaction of ligand/receptor specificity exchangers with mammalian cells. For example, the ability of a ligand/receptor specificity exchanger to interact with an integrin receptor present on a cancer cell can be determined as follows. Melanoma cells that express an $\alpha_v\beta_3$ receptor (e.g., M21 human melanoma cells) bind fibrinogen and this interaction can be blocked by administering an RGD containing peptide (See e.g., Katada et al., *J. Biol. Chem.* 272: 7720 (1997) and Felding-Habermann et al., *J. Biol. Chem.* 271:5892–5900 (1996); both references herein expressly incorporated by reference in their entireties). Similarly, many other types of cancer cells express integrins that interact with RGD peptides. By one approach, cancer cells that expresses an RGD-responsive integrin (e.g., M21 human melanoma cells) are cultured to confluency. M21 cells can be grown in DMEM media with 10% fetal bovine serum, 20 mM Hepes, and 1 mM pyruvate.

Preferably, the cells are stained with hydroethidine (Polysciences, Inc., Warrington, Pa.) at 20 μg/ml final concentration ($2\times10^6$ cells/ml) for 30 min at 37° C. and then washed twice to remove excess dye. Hydroethidine intercalates into the DNA resulting in a red fluorescent labeling of the cells and does not impair the cell's adhesive functions. The staining provides a way to quantify the binding of a ligand/receptor specificity exchanger to the cells. That is, the total number of hydroethidine stained cells can be compared to the number of cells bound to a fluorescently labeled primary antibody/specificity exchanger complex so as to determine the binding efficiency.

Accordingly, the stained cells are incubated with various dilutions of a ligand/receptor specificity exchanger comprising a RGD sequence (e.g., GRGDSPHRGGPEE (SEQ. ID No. 104) or WSRGDWHRGGPEE (SEQ. ID No. 105)). After a 60 minute incubation, the non-bound ligand/receptor specificity exchanger is removed by several washes in DMEM media with 10% fetal bovine serum, 20 mM Hepes, and 1 mM pyruvate (e.g., 3 washes of 5 ml of media). Next, a 1:100–1:1000 dilution of a primary antibody that interacts with the antigenic domain of the ligand/receptor specificity exchanger (e.g., mAb for herpes simplex virus gG2 protein) is provided and the binding reaction is allowed to occur for 60 minutes. Subsequently, several washes in media are performed to remove any non-bound primary antibody. Appropriate controls include stained cells without ligand/receptor specificity exchanger or stained cells without primary antibody.

Following binding of the primary antibody, a goat anti-mouse FITC labeled antibody (1:100 dilution) (Sigma) is added and binding is allowed to occur for 60 minutes. Again, several media washes are made to remove any non-bound secondary antibody. Analysis is made by flow cytometry with filter settings at 543/590 nm for hydroethidine and 495/525 nm for fluorescin. One will observe an appreciable binding of primary antibody to the ligand/receptor specificity exchanger/cell complex, which will demonstrate that the ligand/receptor specificity exchanger will have an effect on the cell. The next section describes characterization assays that are performed in animals.

In Vivo Characterization Assays

Characterization assays also include experiments that evaluate ligand/receptor specificity exchangers in vivo. There are many animal models that are suitable for evaluating the ability of a ligand/receptor specificity exchanger to inhibit pathogenic infection. Mice are preferred because they are easy to maintain and are susceptible to bacterial infection, viral infection, and cancer. Chimpanzees are also preferred because of their close genetic relationship to humans. An approach to evaluate the efficacy of a ligand/receptor specificity exchanger in mice is provided in the next example.

EXAMPLE 3

To test the ability of a ligand/receptor specificity exchanger to treat a bacterial infection the following characterization assay can be performed. Several female CF-1 outbred mice (Charles Rivers Laboratories) of approximately 8 weeks of age and 25 gram body mass are vaccinated with the antigenic domains of the ligand/receptor specificity exchangers to be tested. Preferably, the antigenic domains are coupled to a carrier and are administered with an adjuvant. For example, the antigenic domains can be fused to keyhole limpet hemocyanin or bovine serum albumin, which act as both a carrier and adjuvant or an adjuvant such as Freund's adjuvant, aluminum hydroxide, or lysolecithin can be used. Once a high titer of antibody to the antigenic domains can be verified by, for example, immunodiffusion or EIA, the immunized mice are inoculated intraperitoneally with overnight cultures of *Staphylococcus aureus* NTCC 10649. The inoculums are adjusted to yield approximately $100\times LD_{50}$ or log 6.6 for *S. aureus.*

Serial dilutions of ligand/receptor specificity exchangers (e.g., the ligand/receptor specificity exchangers provide in TABLE III) are formulated in sterile water for injection and are administered by the subcutaneous (SC) or oral (PO) route at one and five hours post infection. Concurrently with each trial, the challenge $LD_{50}$ is validated by inoculation of untreated mice with log dilutions of the bacterial inoculum. Preferably, a five log dilution range of the bacterial challenges is inoculated into five groups of ten mice each (ten mice per log dilution). A mortality rate of 100% will be produced in all groups of untreated mice at the $100\times LD_{50}$ challenge inoculum. Mice are monitored daily for mortality for seven days. The mean effective dose to protect 50% of the mice ($ED_{50}$) can be calculated from cumulative mortality by logarithmic-probit analysis of a plotted curve of survival versus dosage as described in *Antimicrob. Agents Chemother.* 31: 1768–1774 and *Proc. Soc. Exp. Biol. Med.* 1994, 57, 261–264, each of which are hereby expressly incorporated by reference in their entireties. As one of skill in the art will appreciate, similar approaches can be used to test the ability of ligand/receptor specificity exchangers to inhibit viral infection and cancer.

The ligand/receptor specificity exchangers described herein can be formulated in pharmaceuticals and administered to subjects in need of an agent that inhibits the proliferation of a pathogen. The section below describes several pharmaceuticals comprising ligand/receptor specificity exchangers that interact with a receptor on a pathogen.

Pharmaceuticals Comprising a Ligand/Receptor Specificity Exchanger that Interacts with a Receptor on a Pathogen The ligand/receptor specificity exchangers described herein are suitable for incorporation into pharmaceuticals for administration to subjects in need of a compound that treats or prevents infection by a pathogen. These pharmacologically active compounds can be processed in accordance with conventional methods of galenic pharmacy to produce medicinal agents for administration to mammals including humans. The active ingredients can be incorporated into a pharmaceutical product with and without modification. Further the manufacture of pharmaceuticals or therapeutic agents that deliver the pharmacologically active compounds of this invention by several routes are aspects of the present invention. For example, and not by way of limitation, DNA, RNA, and viral vectors having sequences encoding a ligand/receptor specificity exchanger that interacts with a receptor on a pathogen are used with embodiments of the invention. Nucleic acids encoding a ligand/receptor specificity exchanger can be administered alone or in combination with other active ingredients.

The compounds can be employed in admixture with conventional excipients, i.e., pharmaceutically acceptable organic or inorganic carrier substances suitable for parenteral, enteral (e.g., oral) or topical application that do not deleteriously react with the pharmacologically active ingredients described herein. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more vehicles that can be used are described in *Remmington's Pharmaceutical Sciences*, 15th Edition, Easton:Mack Publishing Company, pages 1405–1412 and 1461–1487(1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like so long as the auxiliary agents does not deleteriously react with the ligand/receptor specificity exchangers.

The effective dose and method of administration of a particular pharmaceutical having a ligand/receptor specificity exchanger can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, the effective dose of a ligand/receptor specificity exchanger can be evaluated using the characterization assays described above. The data obtained from these assays is then used in formulating a range of dosage for use with other organisms, including humans. The dosage of such compounds lies preferably within a range of circulating concentrations that include the ED50 with no toxicity. The dosage varies within this range depending upon type of ligand/receptor specificity exchanger, the dosage form employed, sensitivity of the organism, and the route of administration.

Normal dosage amounts of a ligand/receptor specificity exchanger can vary from approximately 1 to 100,000 micrograms, up to a total dose of about 10 grams, depending upon the route of administration. Desirable dosages include about 250 μg-1 mg, about 50 mg–200 mg, and about 250 mg–500 mg.

In some embodiments, the dose of a ligand/receptor specificity exchanger preferably produces a tissue or blood concentration or both from approximately 0.1 μM to 500 mM. Desirable doses produce a tissue or blood concentration or both of about 1 to 800 μM. Preferable doses produce a tissue or blood concentration of greater than about 10 μM to about 500 μM. Although doses that produce a tissue concentration of greater than 800 μM are not preferred, they can be used. A constant infusion of a ligand/receptor specificity exchanger can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism being treated, and weight or size of the organism; diet, time and frequency of administration, drug combination(s), reaction sensitivities, and tolerance/response to therapy. Short acting pharmaceutical compositions are administered daily or more frequently whereas long acting pharmaceutical compositions are administered every 2 or more days, once a week, or once every two weeks or even less frequently.

Routes of administration of the pharmaceuticals include, but are not limited to, topical, transdermal, parenteral, gastrointestinal, transbronchial, and transalveolar. Transdermal administration is accomplished by application of a cream, rinse, gel, etc. capable of allowing the ligand/receptor specificity exchangers to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the ligand/receptor specificity exchangers described herein that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein expressly incorporated by reference in its entirety.

Compositions having pharmacologically active compounds that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having pharmacologically active compounds that are suitable for transbronchial and transalveolar administration include, but are not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the ligand/receptor specificity exchangers described herein.

Compositions having pharmacologically active compounds that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the ligand/receptor specificity exchanger has been obtained, it can be administered to an organism in need to treat or prevent pathogenic infection.

Aspects of the invention also include a coating for medical equipment such as prosthetics, implants, and instruments. Coatings suitable for use on medical devices can be provided by a gel or powder containing the ligand/receptor specificity exchanger or by a polymeric coating into which a ligand/receptor specificity exchanger is suspended. Suitable polymeric materials for coatings of devices are those that are physiologically acceptable and through which a therapeutically effective amount of the ligand/receptor specificity exchanger can diffuse. Suitable polymers include, but are not limited to, polyurethane, polymethacrylate, polyamide, polyester, polyethylene, polypropylene, pozlystyrene, polytetrafluoroethylene, polyvinyl-chloride, cellulose acetate, silicone elastomers, collagen, silk, etc. Such coatings are described, for instance, in U.S. Pat. No. 4,612,337, herein expressly incorporated by reference in its entirety.

The section below describes methods of treating and preventing disease using the ligand/receptor specificity exchangers described herein.

Treatment and Prevention of Disease using a Ligand/Receptor Specificity Exchanger Pharmaceuticals comprising a ligand/receptor specificity exchanger can be administered to a subject in need to treat and/or prevent infection by a pathogen that has a receptor. Such subjects in need can include individuals at risk of contacting a pathogen or individuals who are already infected by a pathogen. These individuals can be identified by standard clinical or diagnostic techniques.

By one approach, for example, a subject suffering from a bacterial infection is identified as a subject in need of an agent that inhibits proliferation of a pathogen. This subject is then provided a therapeutically effective amount of ligand/receptor specificity exchanger. The ligand/receptor specificity exchanger used in this method comprises a specificity domain that interacts with a receptor present on the bacteria (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein). The ligand/receptor specificity exchanger also comprises an antigenic domain that has an epitope of a pathogen or toxin, preferably, an epitope recognized by high titer antibodies present in the subject in need. It may also be desired to screen the subject in need for the presence of high titer antibodies that recognize the antigenic domain prior to providing the subject the ligand/receptor specificity exchanger. This screening can be accomplished by EIA or ELISA using immobilized antigenic domain or ligand/receptor specificity exchanger, as described above.

Similarly a subject in need of an agent that inhibits viral infection can be administered a ligand/receptor specificity exchanger that recognizes a receptor present on the particular etiologic agent. Accordingly, a subject in need of an agent that inhibits viral infection is identified by standard clinical or diagnostic procedures. Next, the subject in need is provided a therapeutically effective amount of a ligand/receptor specificity exchanger that interacts with a receptor present on the type of virus infecting the individual. As above, it may be desired to determine whether the subject has a sufficient titer of antibody to interact with the antigenic domain of the ligand/receptor specificity exchanger prior to administering the ligand/receptor specificity exchanger.

In the same vein, a subject in need of an agent that inhibits the proliferation of cancer can be administered a ligand/receptor specificity exchanger that interacts with a receptor present on the cancer cell. For example, a subject in need of an agent that inhibits proliferation of cancer is identified by standard clinical or diagnostic procedures; then the subject in need is provided a therapeutically effective amount of a ligand/receptor specificity exchanger that interacts with a receptor present on the cancer cells infecting the subject. As noted above, it may be desired to determine whether the subject has a sufficient titer of antibody to interact with the antigenic domain of the ligand/receptor specificity exchanger prior to administering the ligand/receptor specificity exchanger.

Ligand/receptor specificity exchangers described herein can also be administered to subjects as a prophylactic to prevent the onset of disease. Virtually anyone can be administered a ligand/receptor specificity exchanger described herein for prophylactic purposes, (e.g., to prevent a bacterial infection, viral infection, or cancer). It is desired, however, that subjects at a high risk of contracting a particular disease are identified and provided a ligand/receptor specificity exchanger. Subjects at high risk of contracting a disease include individuals with a family history of disease, the elderly or the young, or individuals that come in frequent contact with a pathogen (e.g., health care practitioners). Accordingly, subjects at risk of becoming infected by a pathogen that has a receptor are identified and then are provided a prophylactically effective amount of ligand/receptor specificity exchanger.

One prophylactic application for the ligand/receptor specificity exchangers described herein concerns coating or cross-linking the ligand/receptor specificity exchanger to a medical device or implant implantable medical devices tend to serve as foci for infection by a number of bacterial species. Such device-associated infections are promoted by the tendency of these organisms to adhere to and colonize the surface of the device. Consequently, there is a considerable need to develop surfaces that are less prone to promote the adverse biological reactions that typically accompany the implantation of a medical device.

By one approach, the medical device is coated in a solution of containing a ligand/receptor specificity exchanger. Prior to implantation, medical devices (e.g., a prosthetic valve) can be stored in a solution of ligand/receptor specificity exchangers, for example. Medical devices can also be coated in a powder or gel having a ligand/receptor specificity exchanger. For example, gloves, condoms, and intrauterine devices can be coated in a powder or gel that contains a specificity exchanger that interacts with a bacterial or viral receptor. Once implanted in the body, these ligand/receptor specificity exchangers provide a prophylactic barrier to infection by a pathogen.

In some embodiments, the ligand/receptor specificity exchanger is immobilized to the medical device. As described above, the medical device is a support to which a ligand/receptor specificity exchanger can be attached. Immobilization may occur by hydrophobic interaction between the ligand/receptor specificity exchanger and the medical device but a preferable way to immobilize a ligand/receptor specificity exchanger to a medical device involves covalent attachment. For example, medical devices can be manufactured with a reactive group that interacts with a reactive group present on the specificity exchanger.

By one approach, a periodate is combined with a ligand/receptor specificity exchanger comprising a 2-aminoalcohol moiety to form an aldehyde-functional exchanger in an aqueous solution having a pH between about 4 and about 9 and a temperature between about 0 and about 50 degrees Celsius. Next, the aldehyde-functional exchanger is combined with the biomaterial surface of a medical device that comprises a primary amine moiety to immobilize the ligand/receptor specificity exchanger on the support surface through an imine moiety. Then, the imine moiety is reacted with a reducing agent to form an immobilized ligand/receptor specificity exchanger on the biomaterial surface through a secondary amine linkage. Other approaches for cross-linking molecules to medical devices, (such as described in U.S. Pat. No. 6,017,741, herein expressly incorporated by reference in its entirety); can be modified to immobilize the ligand/receptor specificity exchanger described herein.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A glycosylated ligand/receptor specificity exchanger comprising:

at least one specificity domain comprising a ligand for a bacterial adhesion receptor; and at least one antigenic domain joined to said specificity domain.

2. The ligand/receptor specificity exchanger of claim 1, wherein said ligand is a fragment of fibrinogen.

3. The ligand/receptor specificity exchanger of claim 1, wherein said bacterial adhesion receptor is a *Staphylococcal* adhesion receptor.

4. The ligand/receptor specificity exchanger of claim 3, wherein said *Staphylococcal* adhesion receptor is selected from the group consisting of ClfA, ClfB, Efb, and Fbe.

5. The ligand/receptor specificity exchanger of claim 4, wherein said wherein said *Staphylococcal* adhesion receptor is ClfA or ClfB.

6. The ligand/receptor specificity exchanger of claim 4, wherein said wherein said *Staphylococcal* adhesion receptor is ClfA.

7. The ligand/receptor specificity exchanger of claim 1, wherein said ligand is between 3 and 20 amino acids in length.

8. A ligand/receptor specificity exchanger comprising a plurality of saccharides and at least one specificity domain joined to at least one antigenic domain, wherein said specificity domain comprises a ligand for a bacterial adhesion receptor.

9. The ligand/receptor specificity exchanger of claim 8, wherein said ligand is a fragment of fibrinogen.

10. The ligand/receptor specificity exchanger of claim 8, wherein said bacterial adhesion receptor is a *Staphylococcal* adhesion receptor.

11. The ligand/receptor specificity exchanger of claim 10, wherein said *Staphylococcal* adhesion receptor is selected from the group consisting of ClfA, ClfB, Efb, and Fbe.

12. The ligand/receptor specificity exchanger of claim 11, wherein said wherein said *Staphylococcal* adhesion receptor is ClfA or ClfB.

13. The ligand/receptor specificity exchanger of claim 11, wherein said wherein said *Staphylococcal* adhesion receptor is ClfA.

14. The ligand/receptor specificity exchanger of claim 8, wherein said ligand is between 3 and 20 amino acids in length.

15. A ligand/receptor specificity exchanger comprising at least one specificity domain joined to at least one antigenic domain, wherein said specificity domain comprises a ligand for a bacterial adhesion receptor and said ligand/receptor specificity exchanger is joined to a saccharide support.

16. The ligand/receptor specificity exchanger of claim 15, wherein said ligand is a fragment of fibrinogen.

17. The ligand/receptor specificity exchanger of claim 15, wherein said bacterial adhesion receptor is a *Staphylococcal* adhesion receptor.

18. The ligand/receptor specificity exchanger of claim 17, wherein said *Staphylococcal* adhesion receptor is selected from the group consisting of ClfA, ClfB, Efb, and Fbe.

19. The ligand/receptor specificity exchanger of claim 18, wherein said wherein said *Staphylococcal* adhesion receptor is ClfA or ClfB.

20. The ligand/receptor specificity exchanger of claim 18, wherein said wherein said *Staphylococcal* adhesion receptor is ClfA.

21. The ligand/receptor specificity exchanger of claim 15, wherein said ligand is between 3 and 20 amino acids in length.

* * * * *

UNITED STATES PATENT AND TRADEMARK OFFICE

CERTIFICATE OF CORRECTION

PATENT NO. : 7,019,111 B2 Page 1 of 1
APPLICATION NO. : 10/608541
DATED : March 28, 2006
INVENTOR(S) : Matti Sällberg It is certified that error appears in the above-identified patent and that said Letters Patent is hereby corrected as shown below:

Column 70, line 66, in Claim 5, after “wherein said” delete second occurrence “wherein said”

Column 71, line 2, in Claim 6, after “wherein said” delete second occurrence “wherein said”

Column 71, line 21, in Claim 12, after “wherein said” delete second occurrence “wherein said”

Column 71, line 24, in Claim 13, after “wherein said” delete second occurrence “wherein said”

Column 72, line 17, in Claim 19, after “wherein said” delete second occurrence “wherein said”

Column 72, line 19, in Claim 20, after “wherein said” delete second occurrence “wherein said”

Signed and Sealed this

Fourteenth Day of November, 2006

JON W. DUDAS

*Director of the United States Patent and Trademark Office*

SEQUENCE LISTING

<160> NUMBER OF SEQ ID NOS: 105
<210> SEQ ID NO 1
<211> LENGTH: 18
<212> TYPE: PRT
<213> ORGANISM: Artificial Sequence
<220> FEATURE:
<223> OTHER INFORMATION: Specificity domain peptide

<400> SEQUENCE: 1

```
Tyr Gly Glu Gly Gln Gln His His Leu Gly Gly Ala Lys Gln Ala Gly
 1               5                  10                  15

Asp Val
```

<210> SEQ ID NO 2
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 2

```
Met Ser Trp Ser Leu His Pro Arg Asn Leu Ile Leu Tyr Phe Tyr Ala
 1               5                  10                  15

Leu Leu Phe Leu
            20
```

<210> SEQ ID NO 3
<211> LENGTH: 19
<212> TYPE: PRT
<213> ORGANISM: Artificial Sequence
<220> FEATURE:
<223> OTHER INFORMATION: Specificity domain peptide

<400> SEQUENCE: 3

```
Ile Leu Tyr Phe Tyr Ala Leu Leu Phe Leu Ser Thr Cys Val Ala Tyr
 1               5                  10                  15

Val Ala Thr
```

<210> SEQ ID NO 4
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 4

```
Ser Ser Thr Cys Val Ala Tyr Val Ala Thr Arg Asp Asn Cys Cys Ile
 1               5                  10                  15

Leu Asp Glu Arg
            20
```

<210> SEQ ID NO 5
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 5

```
Arg Asp Asn Cys Cys Ile Leu Asp Glu Arg Phe Gly Ser Tyr Cys Pro
 1               5                  10                  15

Thr Thr Cys Gly
```

-continued

```
            20


<210> SEQ ID NO 6
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 6

Phe Gly Ser Tyr Cys Pro Thr Thr Cys Gly Ile Ala Asp Phe Leu Ser
 1               5                  10                  15

Thr Tyr Gln Thr
            20


<210> SEQ ID NO 7
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 7

Ile Ala Asp Phe Leu Ser Thr Tyr Gln Thr Lys Val Asp Lys Asp Leu
 1               5                  10                  15

Gln Ser Leu Glu
            20


<210> SEQ ID NO 8
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 8

Lys Val Asp Lys Asp Leu Gln Ser Leu Glu Asp Ile Leu His Gln Val
 1               5                  10                  15

Glu Asn Lys Thr
            20


<210> SEQ ID NO 9
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 9

Asp Ile Leu His Gln Val Glu Asn Lys Thr Ser Glu Val Lys Gln Leu
 1               5                  10                  15

Ile Lys Ala Ile
            20


<210> SEQ ID NO 10
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 10

Ser Glu Val Lys Gln Leu Ile Lys Ala Ile Gln Leu Thr Tyr Asn Pro
 1               5                  10                  15
```

-continued

```
Asp Glu Ser Ser
            20


<210> SEQ ID NO 11
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 11

Gln Leu Thr Tyr Asn Pro Asp Glu Ser Ser Lys Pro Asn Met Ile Asp
 1               5                  10                  15

Ala Ala Thr Leu
            20


<210> SEQ ID NO 12
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 12

Lys Pro Asn Met Ile Asp Ala Ala Thr Leu Lys Ser Arg Ile Met Leu
 1               5                  10                  15

Glu Glu Ile Met
            20


<210> SEQ ID NO 13
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 13

Lys Ser Arg Ile Met Leu Glu Glu Ile Met Lys Tyr Glu Ala Ser Ile
 1               5                  10                  15

Leu Thr His Asp
            20


<210> SEQ ID NO 14
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 14

Lys Tyr Glu Ala Ser Ile Leu Thr His Asp Ser Ser Ile Arg Tyr Leu
 1               5                  10                  15

Gln Glu Ile Tyr
            20


<210> SEQ ID NO 15
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 15

Ser Ser Ile Arg Tyr Leu Gln Glu Ile Tyr Asn Ser Asn Asn Gln Lys
 1               5                  10                  15
```

-continued

```
Ile Val Asn Leu
            20


<210> SEQ ID NO 16
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 16

Asn Ser Asn Asn Gln Lys Ile Val Asn Leu Lys Glu Lys Val Ala Gln
 1               5                  10                  15

Leu Glu Ala Gln
            20


<210> SEQ ID NO 17
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 17

Cys Gln Glu Pro Cys Lys Asp Thr Val Gln Ile His Asp Ile Thr Gly
 1               5                  10                  15

Lys Asp Cys Gln
            20


<210> SEQ ID NO 18
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 18

Ile His Asp Ile Thr Gly Lys Asp Cys Gln Asp Ile Ala Asn Lys Gly
 1               5                  10                  15

Ala Lys Gln Ser
            20


<210> SEQ ID NO 19
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 19

Asp Ile Ala Asn Lys Gly Ala Lys Gln Ser Gly Leu Tyr Phe Ile Lys
 1               5                  10                  15

Pro Leu Lys Ala
            20


<210> SEQ ID NO 20
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 20

Gly Leu Tyr Phe Ile Lys Pro Leu Lys Ala Asn Gln Gln Phe Leu Val
```

-continued

```
 1               5                  10                  15

Tyr Cys Glu Ile
            20


<210> SEQ ID NO 21
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 21

Asn Gln Gln Phe Leu Val Tyr Cys Glu Ile Asp Gly Ser Gly Asn Gly
 1               5                  10                  15

Trp Thr Val Phe
            20


<210> SEQ ID NO 22
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 22

Asp Gly Ser Gly Asn Gly Trp Thr Val Phe Gln Lys Arg Leu Asp Gly
 1               5                  10                  15

Ser Val Asp Phe
            20


<210> SEQ ID NO 23
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 23

Gln Lys Arg Leu Asp Gly Ser Val Asp Phe Lys Lys Asn Trp Ile Gln
 1               5                  10                  15

Tyr Lys Glu Gly
            20


<210> SEQ ID NO 24
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 24

Lys Lys Asn Trp Ile Gln Tyr Lys Glu Gly Phe Gly His Leu Ser Pro
 1               5                  10                  15

Thr Gly Thr Thr
            20


<210> SEQ ID NO 25
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 25
```

-continued

```
Phe Gly His Leu Ser Pro Thr Gly Thr Thr Glu Phe Trp Leu Gly Asn
 1               5                  10                  15

Glu Lys Ile His
            20


<210> SEQ ID NO 26
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 26

Glu Phe Trp Leu Gly Asn Glu Lys Ile His Leu Ile Ser Thr Gln Ser
 1               5                  10                  15

Ala Ile Pro Tyr
            20


<210> SEQ ID NO 27
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 27

Leu Ile Ser Thr Gln Ser Ala Ile Pro Tyr Ala Leu Arg Val Glu Leu
 1               5                  10                  15

Glu Asp Trp Asn
            20


<210> SEQ ID NO 28
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 28

Ala Leu Arg Val Glu Leu Glu Asp Trp Asn Gly Arg Thr Ser Thr Ala
 1               5                  10                  15

Asp Tyr Ala Met
            20


<210> SEQ ID NO 29
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 29

Gly Arg Thr Ser Thr Ala Asp Tyr Ala Met Phe Lys Val Gly Pro Glu
 1               5                  10                  15

Ala Asp Lys Tyr
            20


<210> SEQ ID NO 30
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 30
```

-continued

```
Phe Lys Val Gly Pro Glu Ala Asp Lys Tyr Arg Leu Thr Tyr Ala Tyr
 1               5                  10                  15

Phe Ala Gly Gly
            20


<210> SEQ ID NO 31
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 31

Arg Leu Thr Tyr Ala Tyr Phe Ala Gly Gly Asp Ala Gly Asp Ala Phe
 1               5                  10                  15

Asp Gly Phe Asp
            20


<210> SEQ ID NO 32
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 32

Asp Ala Gly Asp Ala Phe Asp Gly Phe Asp Phe Gly Asp Asp Pro Ser
 1               5                  10                  15

Asp Lys Phe Phe
            20


<210> SEQ ID NO 33
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 33

Phe Gly Asp Asp Pro Ser Asp Lys Phe Phe Thr Ser His Asn Gly Met
 1               5                  10                  15

Gln Phe Ser Thr
            20


<210> SEQ ID NO 34
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 34

Thr Ser His Asn Gly Met Gln Phe Ser Thr Trp Asp Asn Asp Asn Asp
 1               5                  10                  15

Lys Phe Glu Gly
            20


<210> SEQ ID NO 35
<211> LENGTH: 20
<212> TYPE: PRT
<213> ORGANISM: Artificial Sequence
<220> FEATURE:
<223> OTHER INFORMATION: Specificity domain peptide
```

-continued

<400> SEQUENCE: 35

Trp Asp Asn Asp Asn Asp Lys Phe Glu Gly Asn Cys Ala Glu Gln Asp
1 5 10 15

Gly Ser Gly Trp
20

<210> SEQ ID NO 36
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 36

Asn Cys Ala Glu Gln Asp Gly Ser Gly Trp Trp Met Asn Lys Cys His
1 5 10 15

Ala Gly His Leu
20

<210> SEQ ID NO 37
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 37

Trp Met Asn Lys Cys His Ala Gly His Leu Asn Gly Val Tyr Tyr Gln
1 5 10 15

Gly Gly Thr Tyr
20

<210> SEQ ID NO 38
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 38

Asn Gly Val Tyr Tyr Gln Gly Gly Thr Tyr Ser Lys Ala Ser Thr Pro
1 5 10 15

Asn Gly Tyr Asp
20

<210> SEQ ID NO 39
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 39

Ser Lys Ala Ser Thr Pro Asn Gly Tyr Asp Asn Gly Ile Ile Trp Ala
1 5 10 15

Thr Trp Lys Thr
20

<210> SEQ ID NO 40
<211> LENGTH: 20
<212> TYPE: PRT
<213> ORGANISM: Artificial Sequence
<220> FEATURE:
<223> OTHER INFORMATION: Specificity domain peptide -continued

<400> SEQUENCE: 40

Asn Gly Ile Ile Trp Ala Thr Trp Lys Thr Arg Trp Tyr Ser Met Lys
1 5 10 15

Lys Thr Thr Met
20

<210> SEQ ID NO 41
<211> LENGTH: 20
<212> TYPE: PRT
<213> ORGANISM: Artificial Sequence
<220> FEATURE:
<223> OTHER INFORMATION: Specificity domain peptide

<400> SEQUENCE: 41

Arg Trp Tyr Ser Met Lys Lys Thr Thr Met Lys Ile Ile Pro Phe Asn
1 5 10 15

Arg Leu Thr Ile
20

<210> SEQ ID NO 42
<211> LENGTH: 27
<212> TYPE: PRT
<213> ORGANISM: Artificial Sequence
<220> FEATURE:
<223> OTHER INFORMATION: Specificity domain peptide

<400> SEQUENCE: 42

Lys Ile Ile Pro Phe Asn Arg Leu Thr Ile Gly Glu Gly Gln Gln His
1 5 10 15

His Leu Gly Gly Ala Lys Gln Ala Gly Asp Val
20 25

<210> SEQ ID NO 43
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 43

Gly Leu Tyr Ser Ser Ile Trp Leu Ser Pro Gly Arg Ser Tyr Phe Glu
1 5 10 15

Thr

<210> SEQ ID NO 44
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 44

Tyr Thr Asp Ile Lys Tyr Asn Pro Phe Thr Asp Arg Gly Glu Gly Asn
1 5 10 15

Met

<210> SEQ ID NO 45
<211> LENGTH: 17
<212> TYPE: PRT
<213> ORGANISM: Artificial Sequence
<220> FEATURE:
<223> OTHER INFORMATION: Antigenic domain peptide -continued

<400> SEQUENCE: 45

```
Asp Gln Asn Ile His Met Asn Ala Arg Leu Leu Ile Arg Ser Pro Phe
 1               5                  10                  15

Thr
```

<210> SEQ ID NO 46
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 46

```
Leu Ile Arg Ser Pro Phe Thr Asp Pro Gln Leu Leu Val His Thr Asp
 1               5                  10                  15

Pro
```

<210> SEQ ID NO 47
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 47

```
Gln Lys Glu Ser Leu Leu Phe Pro Pro Val Lys Leu Leu Arg Arg Val
 1               5                  10                  15

Pro
```

<210> SEQ ID NO 48
<211> LENGTH: 11
<212> TYPE: PRT
<213> ORGANISM: Artificial Sequence
<220> FEATURE:
<223> OTHER INFORMATION: Antigenic domain peptide

<400> SEQUENCE: 48

```
Pro Ala Leu Thr Ala Val Glu Thr Gly Ala Thr
 1               5                  10
```

<210> SEQ ID NO 49
<211> LENGTH: 8
<212> TYPE: PRT
<213> ORGANISM: Artificial Sequence
<220> FEATURE:
<223> OTHER INFORMATION: Antigenic domain peptide

<400> SEQUENCE: 49

```
Ser Thr Leu Val Pro Glu Thr Thr
 1               5
```

<210> SEQ ID NO 50
<211> LENGTH: 13
<212> TYPE: PRT
<213> ORGANISM: Artificial Sequence
<220> FEATURE:
<223> OTHER INFORMATION: Antigenic domain peptide

<400> SEQUENCE: 50

```
Thr Pro Pro Ala Tyr Arg Pro Pro Asn Ala Pro Ile Leu
 1               5                  10
```

<210> SEQ ID NO 51
<211> LENGTH: 9

-continued

<212> TYPE: PRT
<213> ORGANISM: Artificial Sequence
<220> FEATURE:
<223> OTHER INFORMATION: Antigenic domain peptide

<400> SEQUENCE: 51

Glu Ile Pro Ala Leu Thr Ala Val Glu
 1               5

<210> SEQ ID NO 52
<211> LENGTH: 10
<212> TYPE: PRT
<213> ORGANISM: Artificial Sequence
<220> FEATURE:
<223> OTHER INFORMATION: Antigenic domain peptide

<400> SEQUENCE: 52

Leu Glu Asp Pro Ala Ser Arg Asp Leu Val
 1               5                   10

<210> SEQ ID NO 53
<211> LENGTH: 8
<212> TYPE: PRT
<213> ORGANISM: Artificial Sequence
<220> FEATURE:
<223> OTHER INFORMATION: Antigenic domain peptide

<400> SEQUENCE: 53

His Arg Gly Gly Pro Glu Glu Phe
 1               5

<210> SEQ ID NO 54
<211> LENGTH: 7
<212> TYPE: PRT
<213> ORGANISM: Artificial Sequence
<220> FEATURE:
<223> OTHER INFORMATION: Antigenic domain peptide

<400> SEQUENCE: 54

His Arg Gly Gly Pro Glu Glu
 1               5

<210> SEQ ID NO 55
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 55

Val Leu Ile Cys Gly Glu Asn Thr Val Ser Arg Asn Tyr Ala Thr His
 1               5                   10                  15

Ser

<210> SEQ ID NO 56
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 56

Lys Ile Asn Thr Met Pro Pro Phe Leu Asp Thr Glu Leu Thr Ala Pro
 1               5                   10                  15

Ser

-continued

<210> SEQ ID NO 57
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 57

Pro Asp Glu Lys Ser Gln Arg Glu Ile Leu Leu Asn Lys Ile Ala Ser
1 5 10 15

Tyr

<210> SEQ ID NO 58
<211> LENGTH: 17
<212> TYPE: PRT
<213> ORGANISM: Artificial Sequence
<220> FEATURE:
<223> OTHER INFORMATION: Antigenic domain peptide

<400> SEQUENCE: 58

Thr Ala Thr Thr Thr Thr Tyr Ala Tyr Pro Gly Thr Asn Arg Pro Pro
1 5 10 15

Val

<210> SEQ ID NO 59
<211> LENGTH: 8
<212> TYPE: PRT
<213> ORGANISM: Artificial Sequence
<220> FEATURE:
<223> OTHER INFORMATION: Antigenic domain peptide

<400> SEQUENCE: 59

Ser Thr Pro Leu Pro Glu Thr Thr
1 5

<210> SEQ ID NO 60
<211> LENGTH: 26
<212> TYPE: PRT
<213> ORGANISM: Artificial Sequence
<220> FEATURE:
<223> OTHER INFORMATION: Ligand/Receptor specificity exchanger peptide

<400> SEQUENCE: 60

Tyr Gly Glu Gly Gln Gln His His Leu Gly Gly Ala Lys Gln Ala Gly
1 5 10 15

Asp Val His Arg Gly Gly Pro Glu Glu Phe
20 25

<210> SEQ ID NO 61
<211> LENGTH: 25
<212> TYPE: PRT
<213> ORGANISM: Artificial Sequence
<220> FEATURE:
<223> OTHER INFORMATION: Ligand/Receptor specificity exchanger peptide

<400> SEQUENCE: 61

Tyr Gly Glu Gly Gln Gln His His Leu Gly Gly Ala Lys Gln Ala Gly
1 5 10 15

Asp Val His Arg Gly Gly Pro Glu Glu
20 25

<210> SEQ ID NO 62
<211> LENGTH: 26
<212> TYPE: PRT

-continued

<213> ORGANISM: Artificial Sequence
<220> FEATURE:
<223> OTHER INFORMATION: Ligand/Receptor specificity exchanger peptide

<400> SEQUENCE: 62

```
Tyr Gly Glu Gly Gln Gln His His Leu Gly Gly Ala Lys Gln Ala Gly
 1               5                  10                  15

Asp Val Ser Thr Pro Leu Pro Glu Thr Thr
            20                  25
```

<210> SEQ ID NO 63
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 63

```
Met Ser Trp Ser Leu His Pro Arg Asn Leu Ile Leu Tyr Phe Tyr Ala
 1               5                  10                  15

Leu Leu Phe Leu His Arg Gly Gly Pro Glu Glu
            20                  25
```

<210> SEQ ID NO 64
<211> LENGTH: 26
<212> TYPE: PRT
<213> ORGANISM: Artificial Sequence
<220> FEATURE:
<223> OTHER INFORMATION: Ligand/Receptor specificity exchanger peptide

<400> SEQUENCE: 64

```
Ile Leu Tyr Phe Tyr Ala Leu Leu Phe Leu Ser Thr Cys Val Ala Tyr
 1               5                  10                  15

Val Ala Thr His Arg Gly Gly Pro Glu Glu
            20                  25
```

<210> SEQ ID NO 65
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 65

```
Ser Ser Thr Cys Val Ala Tyr Val Ala Thr Arg Asp Asn Cys Cys Ile
 1               5                  10                  15

Leu Asp Glu Arg His Arg Gly Gly Pro Glu Glu
            20                  25
```

<210> SEQ ID NO 66
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 66

```
Arg Asp Asn Cys Cys Ile Leu Asp Glu Arg Phe Gly Ser Tyr Cys Pro
 1               5                  10                  15

Thr Thr Cys Gly His Arg Gly Gly Pro Glu Glu
            20                  25
```

<210> SEQ ID NO 67
<211> LENGTH: 27

<212> TYPE: PRT
<213> ORGANISM: Artificial Sequence
<220> FEATURE:
<223> OTHER INFORMATION: Ligand/Receptor specificity exchanger peptide

<400> SEQUENCE: 67

```
Phe Gly Ser Tyr Cys Pro Thr Thr Cys Gly Ile Ala Asp Phe Leu Ser
 1               5                  10                  15

Thr Tyr Gln Thr His Arg Gly Gly Pro Glu Glu
            20                  25
```

<210> SEQ ID NO 68
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 68

```
Ile Ala Asp Phe Leu Ser Thr Tyr Gln Thr Lys Val Asp Lys Asp Leu
 1               5                  10                  15

Gln Ser Leu Glu His Arg Gly Gly Pro Glu Glu
            20                  25
```

<210> SEQ ID NO 69
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 69

```
Lys Val Asp Lys Asp Leu Gln Ser Leu Glu Asp Ile Leu His Gln Val
 1               5                  10                  15

Glu Asn Lys Thr His Arg Gly Gly Pro Glu Glu
            20                  25
```

<210> SEQ ID NO 70
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 70

```
Asp Ile Leu His Gln Val Glu Asn Lys Thr Ser Glu Val Lys Gln Leu
 1               5                  10                  15

Ile Lys Ala Ile His Arg Gly Gly Pro Glu Glu
            20                  25
```

<210> SEQ ID NO 71
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 71

```
Ser Glu Val Lys Gln Leu Ile Lys Ala Ile Gln Leu Thr Tyr Asn Pro
 1               5                  10                  15

Asp Glu Ser Ser His Arg Gly Gly Pro Glu Glu
            20                  25
```

<210> SEQ ID NO 72

-continued

<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 72

Gln Leu Thr Tyr Asn Pro Asp Glu Ser Ser Lys Pro Asn Met Ile Asp
1 5 10 15

Ala Ala Thr Leu His Arg Gly Gly Pro Glu Glu
20 25

<210> SEQ ID NO 73
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 73

Lys Pro Asn Met Ile Asp Ala Ala Thr Leu Lys Ser Arg Ile Met Leu
1 5 10 15

Glu Glu Ile Met His Arg Gly Gly Pro Glu Glu
20 25

<210> SEQ ID NO 74
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 74

Lys Ser Arg Ile Met Leu Glu Glu Ile Met Lys Tyr Glu Ala Ser Ile
1 5 10 15

Leu Thr His Asp His Arg Gly Gly Pro Glu Glu
20 25

<210> SEQ ID NO 75
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 75

Lys Tyr Glu Ala Ser Ile Leu Thr His Asp Ser Ser Ile Arg Tyr Leu
1 5 10 15

Gln Glu Ile Tyr His Arg Gly Gly Pro Glu Glu
20 25

<210> SEQ ID NO 76
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 76

Ser Ser Ile Arg Tyr Leu Gln Glu Ile Tyr Asn Ser Asn Asn Gln Lys
1 5 10 15

Ile Val Asn Leu His Arg Gly Gly Pro Glu Glu
20 25

```
<210> SEQ ID NO 77
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 77

Asn Ser Asn Asn Gln Lys Ile Val Asn Leu Lys Glu Lys Val Ala Gln
 1               5                  10                  15

Leu Glu Ala Gln His Arg Gly Gly Pro Glu Glu
            20                  25


<210> SEQ ID NO 78
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 78

Cys Gln Glu Pro Cys Lys Asp Thr Val Gln Ile His Asp Ile Thr Gly
 1               5                  10                  15

Lys Asp Cys Gln His Arg Gly Gly Pro Glu Glu
            20                  25


<210> SEQ ID NO 79
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 79

Ile His Asp Ile Thr Gly Lys Asp Cys Gln Asp Ile Ala Asn Lys Gly
 1               5                  10                  15

Ala Lys Gln Ser His Arg Gly Gly Pro Glu Glu
            20                  25


<210> SEQ ID NO 80
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 80

Asp Ile Ala Asn Lys Gly Ala Lys Gln Ser Gly Leu Tyr Phe Ile Lys
 1               5                  10                  15

Pro Leu Lys Ala His Arg Gly Gly Pro Glu Glu
            20                  25


<210> SEQ ID NO 81
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 81

Gly Leu Tyr Phe Ile Lys Pro Leu Lys Ala Asn Gln Gln Phe Leu Val
 1               5                  10                  15

Tyr Cys Glu Ile His Arg Gly Gly Pro Glu Glu
            20                  25
```

-continued

<210> SEQ ID NO 82
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 82

```
Asn Gln Gln Phe Leu Val Tyr Cys Glu Ile Asp Gly Ser Gly Asn Gly
 1               5                  10                  15

Trp Thr Val Phe His Arg Gly Gly Pro Glu Glu
            20                  25
```

<210> SEQ ID NO 83
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 83

```
Asp Gly Ser Gly Asn Gly Trp Thr Val Phe Gln Lys Arg Leu Asp Gly
 1               5                  10                  15

Ser Val Asp Phe His Arg Gly Gly Pro Glu Glu
            20                  25
```

<210> SEQ ID NO 84
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 84

```
Gln Lys Arg Leu Asp Gly Ser Val Asp Phe Lys Lys Asn Trp Ile Gln
 1               5                  10                  15

Tyr Lys Glu Gly His Arg Gly Gly Pro Glu Glu
            20                  25
```

<210> SEQ ID NO 85
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 85

```
Lys Lys Asn Trp Ile Gln Tyr Lys Glu Gly Phe Gly His Leu Ser Pro
 1               5                  10                  15

Thr Gly Thr Thr His Arg Gly Gly Pro Glu Glu
            20                  25
```

<210> SEQ ID NO 86
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 86

```
Phe Gly His Leu Ser Pro Thr Gly Thr Thr Glu Phe Trp Leu Gly Asn
 1               5                  10                  15

Glu Lys Ile His His Arg Gly Gly Pro Glu Glu
            20                  25
```

-continued

<210> SEQ ID NO 87
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 87

Glu Phe Trp Leu Gly Asn Glu Lys Ile His Leu Ile Ser Thr Gln Ser
1 5 10 15

Ala Ile Pro Tyr His Arg Gly Gly Pro Glu Glu
20 25

<210> SEQ ID NO 88
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 88

Leu Ile Ser Thr Gln Ser Ala Ile Pro Tyr Ala Leu Arg Val Glu Leu
1 5 10 15

Glu Asp Trp Asn His Arg Gly Gly Pro Glu Glu
20 25

<210> SEQ ID NO 89
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 89

Ala Leu Arg Val Glu Leu Glu Asp Trp Asn Gly Arg Thr Ser Thr Ala
1 5 10 15

Asp Tyr Ala Met His Arg Gly Gly Pro Glu Glu
20 25

<210> SEQ ID NO 90
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 90

Gly Arg Thr Ser Thr Ala Asp Tyr Ala Met Phe Lys Val Gly Pro Glu
1 5 10 15

Ala Asp Lys Tyr His Arg Gly Gly Pro Glu Glu
20 25

<210> SEQ ID NO 91
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 91

Phe Lys Val Gly Pro Glu Ala Asp Lys Tyr Arg Leu Thr Tyr Ala Tyr
1 5 10 15

Phe Ala Gly Gly His Arg Gly Gly Pro Glu Glu

-continued

```
            20                  25


<210> SEQ ID NO 92
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 92

Arg Leu Thr Tyr Ala Tyr Phe Ala Gly Gly Asp Ala Gly Asp Ala Phe
 1               5                  10                  15

Asp Gly Phe Asp His Arg Gly Gly Pro Glu Glu
            20                  25


<210> SEQ ID NO 93
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 93

Asp Ala Gly Asp Ala Phe Asp Gly Phe Asp Phe Gly Asp Asp Pro Ser
 1               5                  10                  15

Asp Lys Phe Phe His Arg Gly Gly Pro Glu Glu
            20                  25


<210> SEQ ID NO 94
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 94

Phe Gly Asp Asp Pro Ser Asp Lys Phe Phe Thr Ser His Asn Gly Met
 1               5                  10                  15

Gln Phe Ser Thr His Arg Gly Gly Pro Glu Glu
            20                  25


<210> SEQ ID NO 95
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 95

Thr Ser His Asn Gly Met Gln Phe Ser Thr Trp Asp Asn Asp Asn Asp
 1               5                  10                  15

Lys Phe Glu Gly His Arg Gly Gly Pro Glu Glu
            20                  25


<210> SEQ ID NO 96
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 96

Trp Asp Asn Asp Asn Asp Lys Phe Glu Gly Asn Cys Ala Glu Gln Asp
 1               5                  10                  15
```

-continued

```
Gly Ser Gly Trp His Arg Gly Gly Pro Glu Glu
            20                  25


<210> SEQ ID NO 97
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 97

Asn Cys Ala Glu Gln Asp Gly Ser Gly Trp Trp Met Asn Lys Cys His
 1               5                  10                  15

Ala Gly His Leu His Arg Gly Gly Pro Glu Glu
            20                  25


<210> SEQ ID NO 98
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 98

Trp Met Asn Lys Cys His Ala Gly His Leu Asn Gly Val Tyr Tyr Gln
 1               5                  10                  15

Gly Gly Thr Tyr His Arg Gly Gly Pro Glu Glu
            20                  25


<210> SEQ ID NO 99
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 99

Asn Gly Val Tyr Tyr Gln Gly Gly Thr Tyr Ser Lys Ala Ser Thr Pro
 1               5                  10                  15

Asn Gly Tyr Asp His Arg Gly Gly Pro Glu Glu
            20                  25


<210> SEQ ID NO 100
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 100

Ser Lys Ala Ser Thr Pro Asn Gly Tyr Asp Asn Gly Ile Ile Trp Ala
 1               5                  10                  15

Thr Trp Lys Thr His Arg Gly Gly Pro Glu Glu
            20                  25


<210> SEQ ID NO 101
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 101

Asn Gly Ile Ile Trp Ala Thr Trp Lys Thr Arg Trp Tyr Ser Met Lys
 1               5                  10                  15
```

-continued

```
Lys Thr Thr Met His Arg Gly Gly Pro Glu Glu
            20                  25


<210> SEQ ID NO 102
<211> LENGTH: 27
<212> TYPE: PRT
<213> ORGANISM: Artificial Sequence
<220> FEATURE:
<223> OTHER INFORMATION: Ligand/Receptor specificity exchanger peptide

<400> SEQUENCE: 102

Arg Trp Tyr Ser Met Lys Lys Thr Thr Met Lys Ile Ile Pro Phe Asn
 1               5                  10                  15

Arg Leu Thr Ile His Arg Gly Gly Pro Glu Glu
            20                  25


<210> SEQ ID NO 103
<211> LENGTH: 34
<212> TYPE: PRT
<213> ORGANISM: Artificial Sequence
<220> FEATURE:
<223> OTHER INFORMATION: Ligand/Receptor specificity exchanger peptide

<400> SEQUENCE: 103

Lys Ile Ile Pro Phe Asn Arg Leu Thr Ile Gly Glu Gly Gln Gln His
 1               5                  10                  15

His Leu Gly Gly Ala Lys Gln Ala Gly Asp Val His Arg Gly Gly Pro
            20                  25                  30

Glu Glu


<210> SEQ ID NO 104
<211> LENGTH: 13
<212> TYPE: PRT
<213> ORGANISM: Artificial Sequence
<220> FEATURE:
<223> OTHER INFORMATION: Integrin specific ligand/receptor specificity
      exchanger peptide

<400> SEQUENCE: 104

Gly Arg Gly Asp Ser Pro His Arg Gly Gly Pro Glu Glu
 1               5                  10


<210> SEQ ID NO 105
<211> LENGTH: 13
<212> TYPE: PRT
<213> ORGANISM: Artificial Sequence
<220> FEATURE:
<223> OTHER INFORMATION: Integrin specific ligand/receptor specificity
      exchanger peptide

<400> SEQUENCE: 105

Trp Ser Arg Gly Asp Trp His Arg Gly Gly Pro Glu Glu
 1               5                  10
```